United States Patent [19]
Redei et al.

[11] Patent Number: 6,039,956
[45] Date of Patent: *Mar. 21, 2000

[54] CORTICOTROPIN RELEASE INHIBITING FACTOR AND METHODS OF USING SAME FOR TREATING BEHAVIORAL SYMPTOMS IN AN ANXIETY DISORDER

[75] Inventors: Eva Redei, Chicago; Fraser Aird, Oak Park, both of Ill.; Peter A. Rittenhouse, Philadelphia, Pa.; Robert F. McGivern, San Diego, Calif.

[73] Assignee: Pennsylvania, Trustees of the University of, The, Philadelphia, Pa.

[ * ] Notice: This patent is subject to a terminal disclaimer.

[21] Appl. No.: 08/660,561

[22] Filed: Jun. 7, 1996

Related U.S. Application Data

[63] Continuation-in-part of application No. 08/523,125, Sep. 8, 1995, Pat. No. 5,830,866, which is a continuation-in-part of application No. 08/304,383, Sep. 12, 1994, abandoned.

[51] Int. Cl.$^7$ .................................................. A61K 38/06
[52] U.S. Cl. .......................... 424/198.1; 424/562; 514/12; 514/13; 514/15; 514/17; 514/18; 514/925
[58] Field of Search .................................. 514/12, 13, 15, 514/17, 18, 925; 424/198.1, 562

[56] References Cited

U.S. PATENT DOCUMENTS

| | | | |
|---|---|---|---|
| 3,737,549 | 6/1973 | Plotnikoff | 424/274 |
| 3,746,697 | 7/1973 | Folkers | 260/112.5 |
| 3,753,969 | 8/1973 | Folkers | 260/112.5 |
| 3,860,570 | 1/1975 | Thomas et al. | 260/112.5 |
| 3,862,926 | 1/1975 | Fluoret | 260/112.5 |
| 3,873,709 | 3/1975 | Plotnikoff | 514/397 |
| 3,876,624 | 4/1975 | McGregor | 260/112.5 |
| 3,932,623 | 1/1976 | Wilson | 424/177 |
| 4,088,755 | 5/1978 | Inanaga et al. | 424/177 |
| 4,125,605 | 11/1978 | Tyson | 424/177 |
| 4,167,563 | 9/1979 | Mikura et al. | 424/177 |
| 4,215,110 | 7/1980 | Lotti et al. | 424/177 |
| 4,415,558 | 11/1983 | Vale, Jr. et al. | 424/177 |
| 4,489,163 | 12/1984 | Rivier et al. | 436/86 |
| 4,594,329 | 6/1986 | Vale, Jr. et al. | 514/12 |
| 4,605,642 | 8/1986 | Rivier et al. | 514/12 |
| 4,801,612 | 1/1989 | Wei et al. | 514/12 |
| 4,892,813 | 1/1990 | Cohen et al. | 435/4 |
| 5,043,321 | 8/1991 | Baertschi | 514/12 |
| 5,063,245 | 11/1991 | Abreu et al. | 514/404 |
| 5,089,502 | 2/1992 | Sudilovsky et al. | 514/274 |
| 5,109,111 | 4/1992 | Rivier et al. | 530/306 |
| 5,236,901 | 8/1993 | Burks et al. | 514/21 |
| 5,245,009 | 9/1993 | Kornreich et al. | 530/306 |
| 5,278,146 | 1/1994 | Rivier et al. | 514/12 |
| 5,334,702 | 8/1994 | Greene et al. | 530/323 |

FOREIGN PATENT DOCUMENTS

| | | |
|---|---|---|
| 0 067 608 A1 | 12/1982 | European Pat. Off. . |
| 4-352797 | 12/1992 | Japan . |
| 7-8804 | 2/1995 | Japan . |
| 1564078 | 4/1980 | United Kingdom . |
| WO 88/05663 | 8/1988 | WIPO . |
| WO 89/12646 | 12/1989 | WIPO . |
| WO 90/03392 | 4/1990 | WIPO . |
| WO 90/03393 | 4/1990 | WIPO . |
| WO 90/05742 | 5/1990 | WIPO . |
| WO 91/01997 | 2/1991 | WIPO . |
| WO 91/14446 | 10/1991 | WIPO . |
| WO 92/13074 | 8/1992 | WIPO . |
| WO/93/17032 | 9/1993 | WIPO . |

OTHER PUBLICATIONS

Sabol, "Storage and Secretion of β–Endorphin and Related Peptides by Mouse Pituitary Tumor Cells: Regulation by Glucocorticoids" (1980) *Arch. Biochem. Biophys.* 203(1):37–48.

Farah et al., "Paracetamol Interference with Blood Glucose Analysis: A Potentially Fatal Phenomenon" (1982) *Br. Med. J.* 285:172.

Van de Kar et al., "Pharmacological Evidence that Serotonergic Stimulation of Prolaction Secretion is Mediated via the Dorsal Raphe Nucleus" (1982) *Neuroendocrinology* 35:225–230.

Barnett et al., "High Concentrations of Thyroid–Stimulating Hormone in Untreated Glucocorticoid Deficiency: Indication of Primary Hypothyroidism?" (1982) *Br. Med. J.* 285:172–173.

Redei et al., "Hypothalamic Factor of Inhibitory Activity on Pituitary Adrenocortical Function" In: *Integrative Neurohumoral Mechanisms,* (1983) Elsevier Science, Amsterdam 16:377–383.

Yoshida et al., "Isolated ACTH Deficiency Accompanied by 'Primary Hypothyroidism' and Hyperprolactinaemia" (1983) *Acta Endocrinol.* 104:397–401.

Jackson et al., "Immunohistochemical Localization in the Rat Brain of the Precursor for Thyrotropin–Releasing Hormone" (1985) *Science* 229:1097–1099.

Lechan et al., "Thyrotropin–Releasing Hormone Precursor: Characterization in Rat Brain" (1986) *Science* 231:159–161.

Redei et al., "Corticotropin–Inhibiting and Growth Hormone–Releasing Activity in Bovine Hypothalamic Extracts Distinct From Somatostatin and GH–Releasing Hormone" (1986) *AFCR,* Western (Abstract), 1 page.

(List continued on next page.)

*Primary Examiner*—Elizabeth Kemmerer
*Assistant Examiner*—David S. Romeo
*Attorney, Agent, or Firm*—Panitch Schwarze Jacobs & Nadel, P.C.

[57] ABSTRACT

The invention includes a substantially pure preparation of a peptide having corticotropin release inhibiting factor (CRIF) activity comprising at least three contiguous amino acids contained within the amino acid sequence positioned between the fourth and fifth thyrotropin releasing hormone (TRH) sequence on a prepro-TRH protein. The CRIF peptide further comprises the fourth uncleaved TRH portion of prepro-TRH positioned at the amino terminus of CRIF. Compositions, methods of diagnosis and methods of treating CRIF related diseases are also included in the invention.

7 Claims, 23 Drawing Sheets

OTHER PUBLICATIONS

De Nayer et al., "Altered Interaction Between Triiodothyronine and its Nuclear Receptors in Absence of Cortisol: A Proposed Mechanism for Increased Thyrotropin Secretion in Corticosteroid Deficiency States" (1987) *Eur. J. Clin. Invest.* 17:106–110.

Segerson et al., "Thyroid Hormone Regulates TRH Biosynthesis in the Paraventricular Nucleus of the Rat Hypothalamus" (1987) *Science* 238:78–80.

Engler et al., "Studies of the Regulation of the Hypothalamic–Pituitary–Adrenal Axis in Sheep with Hypothalamic–Pituitary Disconnection I. Effect of an Audiovisual Stimulus and Insulin–Induced Hypoglycemia" (1988) *Neuroendocrinology* 48:551–560.

Lee et al., "Structure of the Gene Encoding Rat Thyrotropin Releasing Hormone" (1988) *J. Biol. Chem.* 263(32):16604–16609.

Redei et al., "Effects of Ethanol of CRF Release in Vitro" (1988) *Endocrinology* 123(6):2736–2743.

Wu et al., "Post–Translational Processing of Thyrotropin–Releasing Hormone Precursor in Rat Brain: Identification of 3 novel Peptides Derived from ProTRH" (1988) *Brain Res.* 456:22–28.

Devi et al., "Expression and Posttranslational Processing of Preprodynorphin Complementary DNA in the Mouse Anterior Pituitary Cell Line AtT–20" (1989) *Mol. Endocrinol.* 3(11):1852–1859.

Grossman et al., "The Hunt for the CIA: Factors Which Demonstrates Corticotrophin–Inhibitory Activity" (1989) *J. Endocrinol.* 123:169–172.

Redei et al., "Dual Control of Corticotropin Secretion: Isolation of Corticotropin–Inhibiting Factor" (1989) In: *Neuropeptides and Stress*, Eds. Taché et al., Springer–Verlag, N.Y. (1989) pp. 60–72.

Sanchèz–Franco et al., "Thyroid Hormone Action on ACTH Secretion" (1989) *Horm. Metabol Res.* 21:550–552.

Sevarino et al., "Thyrotropin–Releasing Hormone (TRH) Precursor Processing" (1989) *J. Biol. Chem.* 264:21529–21536.

Sternberg et al., "Inflammatory Mediator–Induced Hypothalamic–Pituitary–Adrenal Axis Activation is Defective in Streptococcal Cell Wall Arthritis–Susceptible Lewis Rats" (1989) *Proc. Natl. Acad. Sci. USA* 86:2374–2378.

Uhler et al., "Complete Amino Acid Sequence of Mouse Pro–Opiomelanocortin Derived from the Nucleotide Sequence of Pro–opiomelanocortin cDNA" (1989) *J. Biol. Chem.* 258(1):257–261.

Bulant et al., "Processing of Thyrotropin–Releasing Hormone (TRH) Prohormone in the Rat Olfactory Bulb Generates Novel TRH–Related Peptides" (1990) *Endocrinology* 127(4):1978–1985.

Yamada et al., "Cloning and Structure of Human Genomic DNA and Hypothalamic CDNA Encoding Human Prepro–Thyrotropin–Releasing Hormone" (1990) *Mol. Endocrinol.* 4(4):551–556.

Karalis et al., "Autocrine or Paracrine Inflammatory Actions of Corticotropin–Releasing Hormone in Vivo" (1991) *Science* 254:421–423.

Plotsky, "Pathways to the Secretion of Adrenocorticotropin: A View from the Portal" (1991) *J. Neuroendocrinol.* 3(1):1–9.

Kakucska et al., "Thyrotropin–Releasing Hormone Gene Expression in the Hypothalamic Paraventricular Nucleus is Dependent Upon Feedback Regulation by Both Triiodothyronine and Thyroxine" (1992) *Endocrinology* 130(5):2845–2850.

Mori et al., "Different Posttranslational Processing of Human PreproThyrotropin–Releasing Hormone in the Human Placenta and Hypothalamus" (1992) *J. Clin. Endocrinol. Metabol.* 75(6):1535–1539.

Satoh et al., "Cloning of the Mouse Hypothalamic Prepro–Thyrotropin–Releasing Hormone (TRH) cDNA and Tissue Distribution of its mRNA" (1992) *Mol. Brain Res.* 14:131–135.

Schlaghecke et al., "Glucocorticoid Receptors in Rheumatoid Arthritis" (1992) *Arthritis Rheum.* 35(7):740–744.

Shigemasa et al., "Evaluation of Thyroid Function in Patients with Isolated Adrenocorticotropin Deficiency" (1992) *Am. J. Med. Sci.* 304(5):279–284.

Carr et al., "A Cryptic Peptide from the PreproThyrotropin–Releasing Hormone Precursor Stimulates Thyrotropin Gene Expression" (1993) *Endocrinology* 133(2):809–814.

Engler, "Evidence that the Hypothalamus Exerts both Stimulatory and Inhibitory Influences Over Adrenocorticotropin Secretion and Biosynthesis in the Sheep" *Reg. Pep.* 45:171–182.

Nillni et al., "Identification of the Thyroptropin–Releasing Hormone Prohormone and its Posttranslational Processing in a Transfected $AtT_{20}$ Tumoral Cell Line" (1993) *Endocrinology* 132(3):1260–1270.

Nillni et al., "Processing of ProTRH to its Intermediate Products Occurs Before the Packing into Secretory Granules of Transfected $AtT_{20}$ Cells" (1993) *Endocrinology* 132(3):1271–1277.

Paré et al., "Depressive Behavior and Stress Ulcer in Wistar Kyoto Rats" (1993) *J. Physiol.* 87:229–238.

Redei et al., "Maternal Adrenalectomy Alters the Immune and Endocrine Functions of the Fetal Alcohol–Exposed Male Offspring" (1993) *Endocrinology* 133(2);452–460.

Redei et al., "Preliminary Evidence for Plasma Adrenocorticotropin Levels as Biological Correlates of Premenstrual Symptoms" (1993) *Acta Endocrinol.* 128:536–542.

Rondeel et al., "Molecular Biology of the Regulation of Hypothalamic Hormones" (1993) *J. Endocrinol. Invest.* 16:219–246.

Wick et al., "Immunoendocrine Communication via the Hypothalamo–Pituitary–Adrenal Axis in Autoimmune Diseases" (1993) *Mol. Endocrinol.* 14(5);539–563.

Palermo et al., "Chronic Anovulation Due to Prolactin Hypersecretion" (1994) *Acta Eur. Fertil.* 25(3):161–172.

Prystowski et al., "Prolactin as a Second Messenger for Interleukin 2" (1994) *Immunomethods* 5:49–55.

Redei et al. Fast Glucocorticoid Feedback Inhibition of ACTH Secretion in the Ovariectomized Rat: Effect of Chronic Estrogen and Progesterone (1994) *Neuroendocrinology* 60:113–123.

Redei et al., "Strain Differences in Hypothalamic–Pituitary–Adrenal Activity and Stress Ulcer" (1994) *Am. J. Physiol.* 266 (Regulatory Integrative Comp. Physiol. 35):R353–360.

Shi et al., "Thyroid Hormone–Mediated Regulation of Corticotropin–Releasing Hormone Messenger Ribonucleic Acid in the Rat" (1994) *Endocrinology* 134(3):1577–1580.

Silman, "Epidemiology of Rheumatoid Arthritis" (1994) *APMIS* 102(10):721–728.

Zumoff, "Hormonal Profiles in Women with Breast Cancer" (1994) *Obstet. Gynecol. Clin. N. Amer.* 21(4):751–772.

Rittenhouse et al., "Thyroid Status Alters Inflammatory Responses to Streptococcal Cell Wall Administration: TRH, POMC and MIP–1α mRNA Expression" (1995) 77th Annual Endocrine Society Meeting P1–677:282.

Walker et al., "Prolactin: A Stimulator of Disease Activity in Systemic Lupus Erythematosus" (1995) *Lupus* 4:3–9.

Redei E; Hilderbrand H; Aird F. Corticotropin release–inhibiting factor is preprothyrotropin–releasing hormone–(178–199). Endocrinology, (Aug. 1995) 136 (8) 3557–63.

FIG. 10

Amino Acid Sequence

RatCRIF

Prepro rat TRH 178-199

Phe-Ile-Asp-Pro-Glu-Leu-Gln-Arg-Ser-Trp-Glu-Glu-Lys-Glu-Gly-Glu-Gly-Val-Leu-Met-Pro-Glu

Prepro rat TRH 172-199 (including 3 amino acids of TRH-pGlu-His-Pro)

pGlu-His-Pro-Gly-Arg-Arg-.....(prepro-TRH 178-199)

Human corresponding sequences:

Prepro human TRH 158-183; 53.8% homology with the rat CRIF sequence

Leu-Ala-Asp-Pro-Lys-Ala-Gln-Arg-Ser-Trp-Glu-Glu-Glu-Glu-Glu-Glu-Glu-Glu-Arg-Glu-Glu-Asp-Leu-Met-Pro-Glu

Possible uncleaved TRH: prepro-human TRH 152-183 pGlu-His-Pro-Gly-Arg-Arg-.....(prepro-human TRH 158-183)

Mouse corresponding sequences:

Prepro-mouse TRH 178-200; 87% homology with the rat CRIF sequence

Phe-Ile-Asp-Pro-Glu-Leu-Gln-Arg-Ser-Trp-Glu-Glu-Thr-Glu-Gly-Glu-Glu-Gly-Gly-Leu-Met-Pro-Glu

Possible uncleaved TRH: prepro mouse TRH 172-200 pGlu-His-Pro-Gly-Arg-Arg-.....(prepro-mouse TRH 178-200)

DNA Sequence

Rat: 172-199

CAACATCCAGGCCGGAGGTTCATAGATCCCGAGCTCCAAAGAAGCTGGGAAG
AAAAAGAGGGAGAGGGTGTCTTAATGCCTGAG

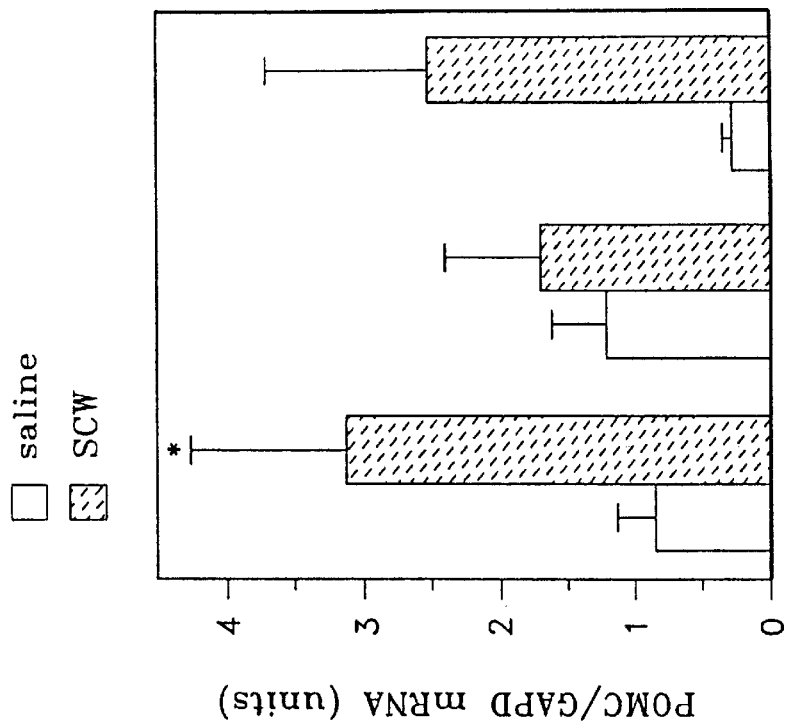
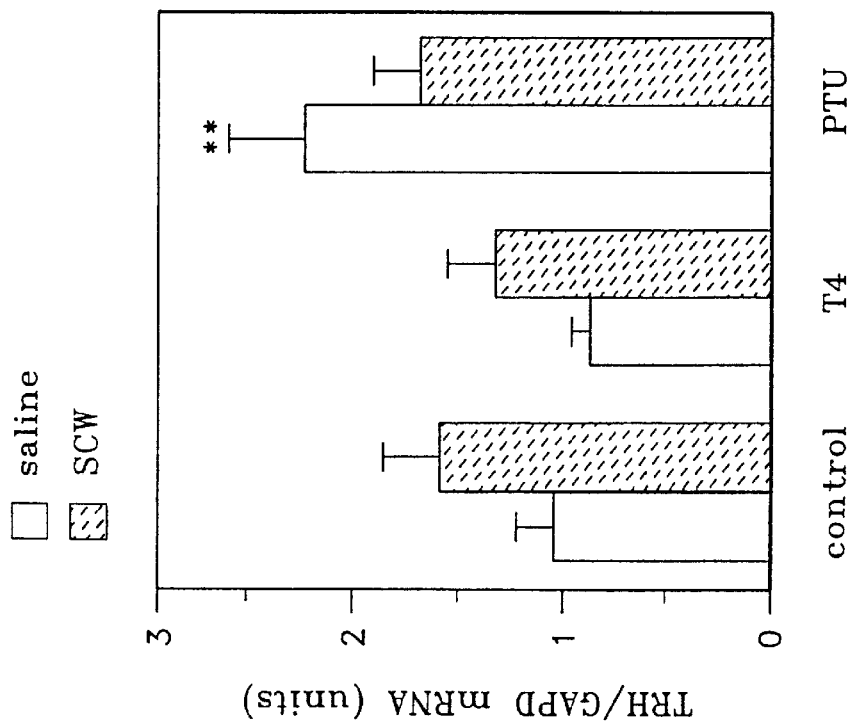
FIG. 12B
FIG. 12A

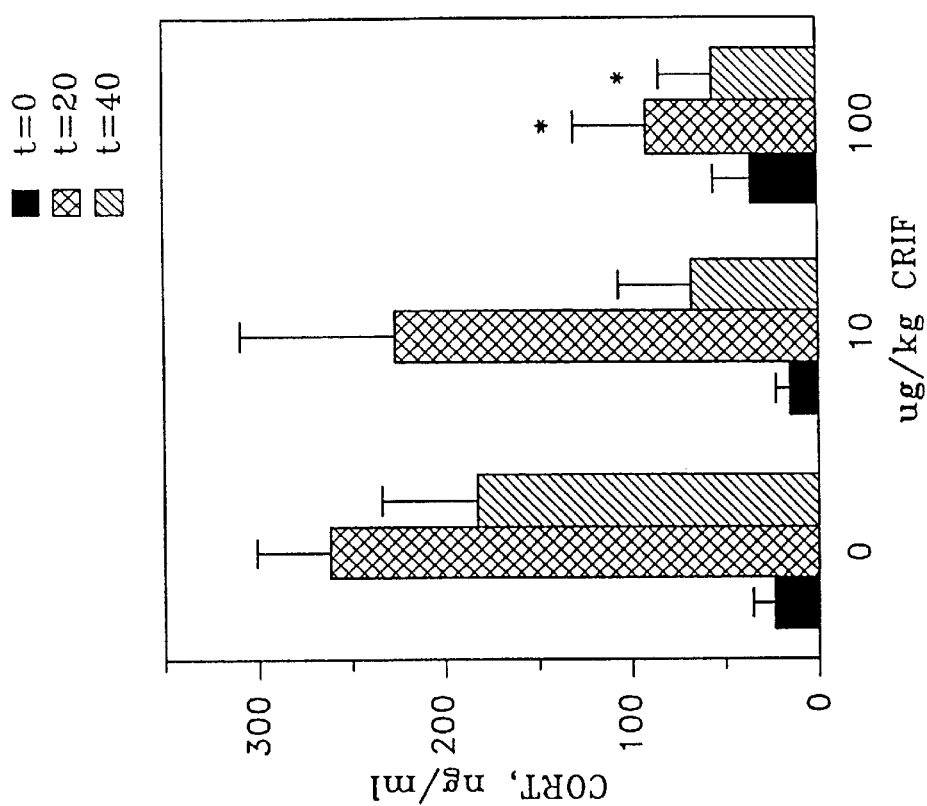
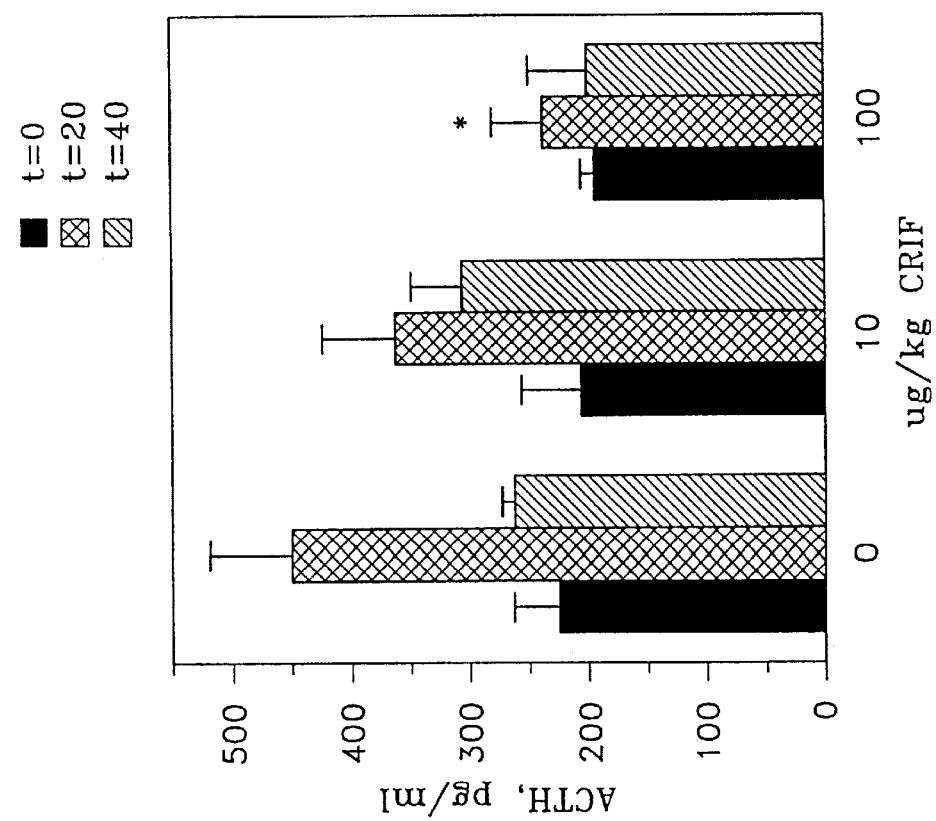
FIG. 14A
FIG. 14B

CORTICOTROPIN RELEASE INHIBITING FACTOR AND METHODS OF USING SAME FOR TREATING BEHAVIORAL SYMPTOMS IN AN ANXIETY DISORDER

CROSS REFERENCE TO RELATED APPLICATIONS

This is a continuation-in-part of application Ser. No. 08/523,125, U.S. Pat. No. 5,830,866, filed on Sep. 8, 1995, which is a continuation-in-part of application Ser. No. 08/304,383, filed on Sep. 12, 1994, abandoned.

GOVERNMENT SUPPORT

This invention was supported in part by funds from the U.S. Government (NIAAA 06478) and the U.S. Government may have certain rights in the invention.

FIELD OF THE INVENTION

This invention relates to modulation of stress and stress-related disorders in a mammal.

BACKGROUND OF THE INVENTION

The onset and/or severity of illness in mammals is related to the level of stress experienced by that mammal. In patients who are ill, either hypo- or hyperactivity of the hypothalamic-pituitary-adrenocortical (HPA) axis has been observed, which activity represents the physiological regulator of the stress response in mammals.

Regulation of HPA occurs via a multifaceted integrated mechanism, wherein corticotropin-releasing factor (CRF) and vasopressin (AVP) produced by the brain are believed to stimulate production of adrenocorticotropin tropin (ACTH) from the anterior pituitary, the primary inducer of cortisol secretion. Cortisol so produced has a negative influence upon ACTH secretion thus providing a feedback regulatory mechanism within this system.

An additional ACTH-inhibiting factor is postulated by Grossman and Tsagarakis (1989, J. Endocrinology, 123:169–172), which is termed corticotropin release inhibiting factor (CRIF or CIF), see Redei et al., In: Neuropeptides and Stress, Eds. Tache et al., Hans Selye Symposia on Neuroendocrinology and Stress, 1989, Springer-Verlag, New York). This activity comprises an unidentified hypothalamic peptide, which peptide exhibits inhibitory activity on basal and CRF or stress stimulated ACTH secretion both in vitro and in vivo (Redei et al., 1984, In: Integrative Neurohormonal Mechanism Developments in Neuroscience, Vol. 16, Eds. Endroczi et al, Elsevier, Amsterdam).

A hypothalamic peptide fraction isolated from both pigs and rats was found to contain CRIF activity. When injected into rats, it suppressed corticosterone (CORT) response to footshock (Redei et al., 1984, In: Integrative Neurohormonal Mechanism Developments in Neuroscience, Vol. 16, Eds. Endroczi et al, Elsevier, Amsterdam). In addition, a peptide fraction (molecular weight 0.6–2.3 kDa) has been isolated from bovine hypothalamus which exhibits CRIF activity both in vitro and in vivo (Redei et al., In: Neuropeptides and Stress, Eds. Tache et al., Hans Selye Symposia on Neuroendocrinology and Stress, 1989, Springer-Verlag, New York).

There has been a long felt need to determine the identity of CRIF because of its important relationship in regulating ACTH production. Compounds which act as agonists or antagonists of CRIF activity, or CRIF itself, are useful for diagnosis and treatment of a variety of diseases associated with stress responses. Such diseases include, but are not limited to, depression, obsessive compulsive disorders, anxiety, withdrawal from drug addiction, autoimmune diseases and even premenstrual syndrome. Such diseases also include cancers whose initiation and/or progression are influenced by the mental state of the individual, which mental state is a reflection of the level of compounds, such as hormones and glucocorticoids, which are either over- or underproduced in that individual. The level of these compounds may be affected by CRIF or a CRIF agonist or antagonist.

In addition, such CRIF peptides and nucleic acids and antibodies related thereto are useful as diagnostic reagents for determination of CRIF-related disease states.

SUMMARY OF THE INVENTION

The invention includes a substantially pure preparation of a CRIF peptide having CRIF activity, which peptide comprises at least three contiguous amino acids contained within the amino acid sequences positioned between the fourth and fifth thyrotropin releasing hormone (TRH) sequence on a prepro-TRH protein.

In one embodiment, the CRIF peptide of the invention comprises at least five amino acids and in another embodiment, the CRIF peptide of the invention comprises at least ten amino acids.

In yet another embodiment, the CRIF peptide of the invention is rat CRIF and preferably the rat CRIF comprises the sequence Phe-Ile-Asp-Pro-Glu-Leu-Gln-Arg-Ser-Trp-Glu-Glu-Lys-Glu-Gly-Glu-Gly-Val-Leu-Met-Pro-Glu [SEQ ID NO:1]. In a further embodiment, the CRIF peptide is human CRIF preferably comprising the sequence Leu-Ala-Asp-Pro-Lys-Ala-Gln-Arg-Ser-Trp-Glu-Glu-Glu-Glu-Glu-Glu-Glu-Glu-Arg-Glu-Glu-Asp-Leu-Met-Pro-Glu [SEQ ID NO:2]; and, in yet another embodiment, the CRIF peptide of the invention is mouse CRIF preferably comprising the sequence Phe-Ile-Asp-Pro-Glu-Leu-Gln-Arg-Ser-Trp-Glu-Glu-Thr-Glu-Gly-Glu-Glu-Gly-Gly-Leu-Met-Pro-Glu [SEQ ID NO:3]. Preferably, the peptide of the invention is in a pharmaceutically acceptable carrier or diluent.

The CRIF peptide of the invention further comprises the sequence pGlu-His-Pro-Gly-Arg-Arg [SEQ ID NO:4] at the amino terminal portion of the peptide. This sequence comprises the fourth uncleaved TRH moiety in prepro-TRH.

By a peptide having CRIF activity is meant a peptide capable of reducing both basal and CRF-stimulated levels of ACTH production in mammalian cells, preferably AtT-20 cells. The CRIF peptide of the invention should also be construed to include peptides comprising the amino acid sequence of CRIF which may be modified in order that it is more stable than the native peptide when used as a diagnostic reagent or as a therapeutic agent. Also included are peptidometics having CRIF activity.

In another aspect of the invention, there is provided an isolated DNA encoding a CRIF peptide having CRIF activity comprising at least three contiguous amino acids contained within the amino acid sequences positioned between the fourth and fifth TRH sequence on a prepro-TRH protein.

In a preferred embodiment, the CRIF is rat CRIF comprising the sequence 5'-TTCATAGATCCCGAGCTCCA-AAGAAGCTGGGAAGAAAAAGAGGGAGAGGGTG-TCTTAATGCCTGAG-3' [SEQ ID NO:5]. In yet another preferred embodiment, the CRIF is human CRIF comprising the sequence 5'-CTGGCAGATCCCAAGGCTCAAAGG-AGCTGGGAAGAAGAGGAGGAGGAGGAAGAGAG-AGAGGAAGACCTGATGCCTGAA-3' [SEQ ID NO:6];

and in yet another preferred embodiment, the CRIF is mouse CRIF comprising the sequence 5'-TTCATAGATCCTGA-GCTCCAAAGAAGCTGGGAAGAAACAGAGGGAGA-GGAGGGTGGCTTAATGCCTGAG-3' [SEQ ID NO:7].

In another embodiment, the sequence encoding CRIF includes a sequence encoding uncleaved TRH at the 5'end. When the CRIF is rat CRIF the sequence comprises 5'-CAACATCCAGGCCGGAGGTTCATAGATCCCGAG-CTCCAAAGAAGCTGGGAAGAAAAAGAGGGAGAG-GGTGTCTTAATGCCTGAG-3' [SEQ ID NO:8]; when the CRIF is human CRIF, the sequence comprises 5'-CAGCACCCAGGCAGAAGGCTGGCAGATCCCAA-GGCTCAAAGGAGCTGGGAAGAAGAGGAGGAGGA-GGAAGAGAGAGAGGAAGACCTGATGCCTGAA-3' [SEQ ID NO:9]; and, when the CRIF is mouse CRIF, the sequence comprises 5'-CAGCATCCAGGCCGGAGGTT-CATAGATCCTGAGCTCCAAAGAAGCTGGGAAGAA-ACAGAGGGAGAGGAGGGTGGCTTAATGCC-TGAG-3' [SEQ ID NO:10].

In yet another aspect of the invention, there is provided a recombinant cell comprising DNA encoding CRIF peptide, which peptide comprises at least three contiguous amino acids contained within the amino acid sequences positioned between the fourth and fifth TRH sequence on a prepro-TRH protein. Also provided is a recombinant cell comprising DNA encoding CRIF peptide, which peptide further comprises the sequence pGlu-His-Pro-Gly-Arg-Arg at the amino terminal portion of the peptide comprising the fourth uncleaved TRH moiety in prepro-TRH.

The invention further includes a vector comprising an isolated DNA encoding a CRIF peptide having CRIF activity, wherein the peptide comprises at least three contiguous amino acids contained within the amino acid sequences positioned within the fourth and fifth TRH sequence on a prepro-TRH protein. The vector of the invention may also include a sequence encoding uncleaved TRH at the 5' end.

In another aspect, the invention includes a CRIF minigene having CRIF coding sequences placed under the control of a promoter capable of driving CRIF expression, which minigene does not contain TRH sequences.

In another aspect, the invention includes an antagonist, i.e., a composition capable of inhibiting CRIF mediated reduction of basal and CRF stimulated ACTH production by a mammalian cell. The composition preferably comprises an oligonucleotide sequence complementary to a DNA encoding a CRIF peptide having CRIF activity and an oligonucleotide sequence which further comprises eighteen nucleotides complementary to sequences encoding the fourth uncleaved TRH peptide, these eighteen nucleotides being positioned at the 3' end of the oligonucleotide.

In another embodiment, the composition capable of inhibiting CRIF mediated reduction of basal and CRF stimulated ACTH production by a mammalian cell comprises a peptidometic.

In yet another aspect, the invention includes an antibody capable of binding to a CRIF peptide having CRIF activity.

In a further aspect of the invention, there is provided an agonist of CRIF activity which is capable of enhancing CRIF mediated reduction of basal and CRF stimulated ACTH production by a mammalian cell. According to the invention, the agonist or antagonist of of CRIF may be a peptidometic.

The invention also includes a method of diagnosing a CRIF associated disease in a mammal suspected of having the disease. The method involves adding to a sample of blood obtained from the mammal an antibody capable of binding to CRIF, and comparing the amount of antibody bound to the mammal's blood with the amount of antibody bound to a sample of blood obtained from a normal mammal, wherein a lower or a higher amount of antibody bound to the mammal's blood compared with the normal mammal's blood is an indication that the mammal has a CRIF associated disease.

In another aspect, the invention includes a method of diagnosing a CRIF related disease in a mammal suspected of having the disease comprising administering CRIF to the mammal, measuring the levels of ACTH or cortisol in blood obtained from the mammal, and comparing the amount of ACTH or cortisol in the blood of the mammal with the amount of ACTH or cortisol in the blood of a normal CRIF treated mammal, wherein a higher or lower level of ACTH or cortisol in the blood of the mammal compared with the level of ACTH or cortisol in the blood of the normal mammal is an indication that the mammal has a CRIF related disease.

Also included in the invention is a diagnostic kit for measuring the amount of CRIF in the blood of a mammal. The kit includes antibody capable of binding to CRIF and instructions for using the kit. The invention also provides yet another diagnostic kit for measuring the amount of CRIF in the blood of a mammal. This kit includes an oligonucleotide sequence complementary to a DNA encoding a CRIF peptide having CRIF activity and instructions for using the kit.

In yet another aspect of the invention, there is provided a method of treating a mammal with a CRIF disorder. The method involves administering to the mammal CRIF in a pharmaceutically acceptable carrier. In another aspect, a method of treating a mammal with a CRIF disorder is included wherein the method involves administering to the mammal antibody to CRIF in a pharmaceutically acceptable carrier. Yet another method of treating a mammal with a CRIF disorder is provided wherein the method involves administering to the mammal an oligonucleotide sequence complementary to a DNA encoding a CRIF peptide having CRIF activity. The oligonucleotide sequence is provided in a pharmaceutically acceptable carrier.

The invention also includes a method of treating an inflammatory disease in a human by increasing the level of endogenous glucocorticoids in the human. The method comprises administering a CRIF antagonist to the human. Preferably, the CRIF antagonist is anti-CRIF antibody. Either one or more than one CRIF antagonist may be administered according to the method of the invention and whether one or two CRIF antagonists are administered, the method may further include administration of thyroid hormone, which may be $T_3$ or $T_4$.

The invention further includes a method of treating an inflammatory disease in a human by increasing the level of endogenous glucocorticoids in the human, the method comprising administering a thyroid hormone to the human. Preferably, the thyroid hormone is $T_3$ or $T_4$.

Also included in the invention is a method of treating an inflammatory disease in a human by increasing the level of endogenous glucocorticoids in the human. This method of the invention comprises administering a compound having thyroid hormone-like activity to the human. Preferably, the compound has $T_3$- or $T_4$-like activity.

The invention further includes a method of treating a disease associated with increased secretion of prolactin in a human, comprising administering CRIF or a CRIF peptidometic to the human in an amount sufficient to reduce prolactin secretion in the human and thereby alleviate the disease. The CRIF or CRIF peptidometic is administered by a peripheral route, or in the case of CRIF, is packaged so as to be capable of crossing the blood brain barrier. The CRIF peptidometic is formulated so as to be capable of crossing the blood brain barrier when administered by any other route.

The invention also includes a method of treating behavioral symptoms in an anxiety disorder in a human. This method comprises administering CRIF or a CRIF peptidometic to the human in an amount sufficient to alleviate the behavioral symptoms. The anxiety disorder to be treated includes, but is not limited to, general anxiety disorder, panic disorder, obsessive compulsive disorder, post-traumatic stress disorder, among other disorders. In this instance, the CRIF peptide of the invention may be administered directly into the brain of animal or it may also be formulated so as to cross the blood brain barrier. A CRIF peptidometic designed to cross the blood brain barrier is administered by a peripheral route for the purpose of alleviating behavorial symptoms.

The invention also includes a CRIF receptor protein.

The present invention also provides for analogs of peptides having CRIF activity. Analogs can differ from naturally occurring proteins or peptides by conservative amino acid sequence differences or by modifications which do not affect sequence, or by both.

For example, conservative amino acid changes may be made, which although they alter the primary sequence of the protein or peptide, do not normally alter its function. Conservative amino acid substitutions typically include substitutions within the following groups:

glycine, alanine;
valine, isoleucine, leucine;
aspartic acid, glutamic acid;
asparagine, glutamine;
serine, threonine;
lysine, arginine; and
phenylalanine, tyrosine.

Other modifications, which do not normally alter the primary sequence but which may be useful, include in vivo or in vitro chemical derivatization of peptides, e.g., amidation, acetylation, or carboxylation, and modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are peptides which have phosphorylated amino acid residues, e.g., phosphotyrosine, phosphoserine, or phosphothreonine.

Also included are peptides which have been modified using ordinary molecular biological techniques so as to improve their resistance to proteolytic degradation or to optimize solubility properties or to render them more suitable as a therapeutic agent. Analogs of such peptides include those containing residues other than naturally occurring L-amino acids, e.g., D-amino acids or non-naturally occurring synthetic amino acids. The peptides of the invention are not limited to products of any of the specific exemplary processes listed herein.

In addition to substantially full length peptides, the present invention provides for biologically active fragments of CRIF. A CRIF peptide is biologically active if it downregulates both basal and CRF stimulated ACTH secretion in the assays described herein.

As used herein, the term "biologically active fragment of CRIF" will ordinarily be three or more contiguous amino acids, typically at least about five contiguous amino acids, and more typically at least about ten contiguous amino acids.

Novel biological antagonists and agonists of CRIF are also contemplated in the invention. A compound is a biological inhibitor of CRIF if it inhibits the synthesis or function of the naturally occurring CRIF peptide in the assays described herein. A compound is a biological activator of CRIF if it activates the synthesis or function of CRIF in the assays described herein. Naturally occurring compounds are known, such as thyroid hormones and glucocorticoids. However, the invention contemplates other compounds which may now be identified in view of the discovery of CRIF.

As used herein, the term "substantially pure" describes a compound, e.g., a peptide which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of peptides by column chromatography, gel electrophoresis or HPLC analysis. A compound, e.g., a peptide is also substantially purified when it is essentially free of naturally associated components or when it is separated from the native contaminants which accompany it in its natural state.

An "isolated nucleic acid", as used herein, refers to a nucleic acid sequence, segment, or fragment which has been purified from the sequences which flank it in a naturally occurring state, e.g., a DNA fragment which has been removed from the sequences which are normally adjacent to the fragment e.g., the sequences adjacent to the fragment in a genome in which it naturally occurs. The term also applies to nucleic acids which have been substantially purified from other components which naturally accompany the nucleic acid, e.g., RNA or DNA or proteins which naturally accompany it in the cell.

A "recombinant cell", as used herein, refers to a cell having within it one or more copies of an isolated nucleic acid, which nucleic acid is added to the cell by recombinant DNA techniques.

"Complementary" as used herein, refers to the subunit sequence complementarity between two nucleic acid molecules, e.g., two DNA molecules or two RNA molecules. When a subunit position in both of the two molecules is occupied by a complementary monomeric subunit, e.g., if one position in each of two DNA molecules is occupied by adenine and the other is occupied by a thymine, then they are complementary at that position. Similarly, if one position in each of two DNA molecules is occupied by guanine and the other is occupied by a cytosine, then they too are complementary at that position. The degree of complementarity between two sequences is a direct function of the number of positions occupied by complementary bases, e.g., if half (e.g., five positions in a polymer ten subunits in length) of the positions in two compound sequences contain complementary bases then the two sequences share 50% complementarity, if 90% of the positions, e.g., 9 of 10, contain bases complementary to each other, the two sequences share 90% complementarity. By way of example, the DNA sequences 5'ATTGCC3' and 3'GGCGCC5' share 50% complementarity.

BRIEF DESCRIPTION OF THE DRAWINGS

FIG. 10 shows the amino acid and nucleotide sequence of rat CRIF and the human and mouse homologs of rat CRIF. [SEQ ID NOS:1, 4, 2, 4, 3, 4, 5, 6 and 7, in the order in which they appear in the figure].

FIG. 14, comprising parts A and B, is a series of graphs depicting inhibition of ACTH and corticosterone response in vivo in rats exposed to footshock stress following administration of different doses of CRIF. (A) measurement of ACTH levels; (B) measurement of corticosterone levels.

FIG. 15, comprising

FIG. 16, comprising In FIG. 16A activity; in FIG. 16B, active sniffing; in FIG. 16C, grooming; and in FIG. 16D rearing, were measured. In the graphs of FIG. 16, open bars represent vehicle, hatched bars represent 0.6 μg/Kg CRIF, and cross-hatched bars represent 6.0 μg/Kg CRIF.

FIG. 17, comprising (in FIG. 17B) number of compartment entries; and (in FIG. 17C) total time spent in each compartment. In the graphs of FIG. 17, open bars represent vehicle, hatched bars represent 0.6 μg/Kg CRIF, and cross hatched bars represent 6.0 μg/Kg CRIF.

DETAILED DESCRIPTION OF THE PREFERRED EMBODIMENTS

Figure 1:
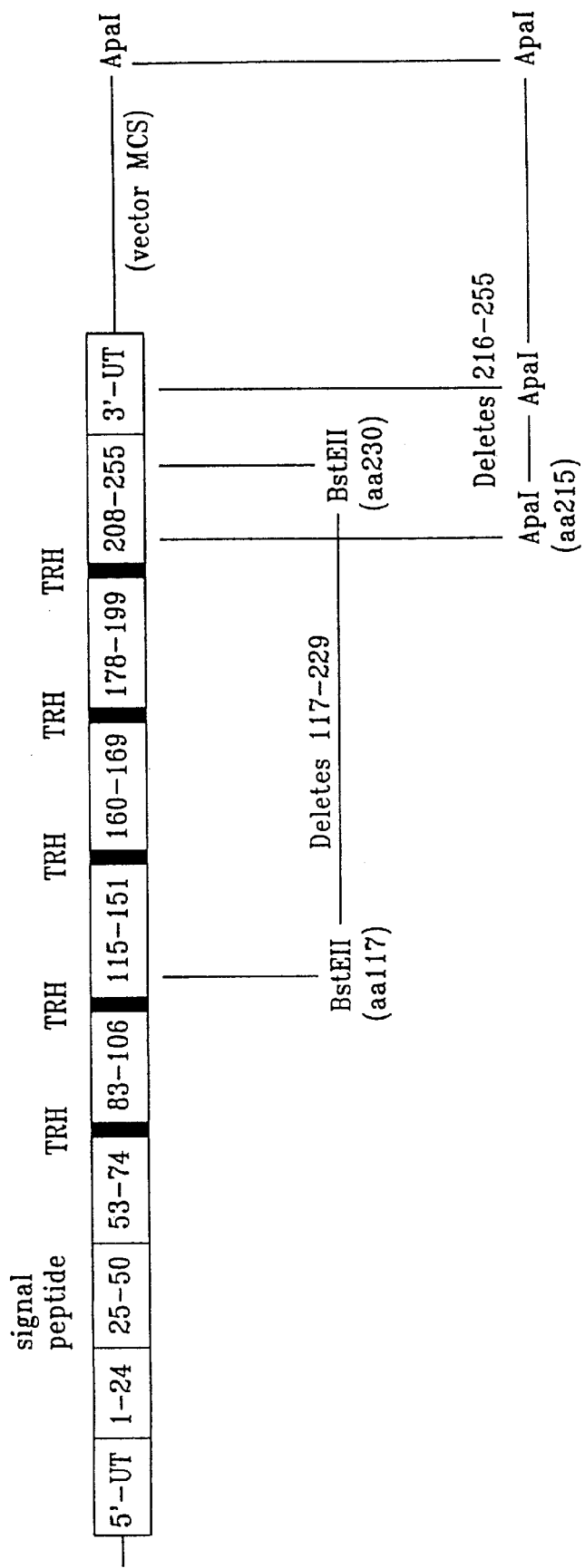
FIG. 1 is a map of the Rat prepro-TRH protein. Groups of amino acids are numbered beginning at the N-terminus of the molecule and the blackened areas indicate the location of each of the five mature TRH tripeptide molecules. The relative positions of the deletions forming plasmids ΔBstEII and ΔApaI span the indicated BstEII and ApaI restriction sites.

The present invention relates to a peptide capable of inhibiting both basal and CRF stimulated production of ACTH in cells, which peptide is identified as CRIF and which comprises a portion of the prepro-TRH molecule. The fact that CRIF and TRH are contained within the same precursor suggests an additional and potentially synchronized level of hypothalamic control of ACTH and thyroid stimulating hormone (TSH). TRH and CRIF have opposing regulatory actions on TSH and ACTH levels, respectively. Thus, when prepro-TRH containing neurons secrete high levels of TRH and consequently high levels of CRIF, the level of TSH in the plasma will rise while the level of ACTH will fall. Conversely, when low levels of TRH and CRIF are synthesized, the level of TSH in plasma is diminished, while the level of ACTH is increased. The former situation is known to occur in hypothyroid states when hypothalamic prepro-TRH levels are increased and the latter situation is known to occur in hyperthyroid states when hypothalamic prepro-TRH levels are decreased.

As the data provided herein establish, CRIF has a marked effect on the inflammatory immune response, on prolactin secretion, on stress and on behavior. CRIF is thus useful for treatment of a variety of disorders. To generate CRIF for use in treating such disorders, CRIF may be produced synthetically using ordinary synthetic peptide techniques available in the art, or CRIF may be produced in cells comprising DNA encoding CRIF. In the latter instance, it is preferable that the cell be either transiently or stably transfected with DNA encoding CRIF, which DNA is placed under the control of a promoter capable of driving high levels of CRIF transcription in that cell. To generate such a cell, a vector is first generated comprising CRIF DNA positioned downstream from a suitable promoter sequence. The promoter sequence to be used is dependent upon the cell into which the DNA is to be transfected. A plethora of promoter sequences are available commercially which may be used to drive gene expression in a variety of eukaryotic and prokaryotic cells. Thus, the choice of promoter sequence to be used will be apparent to the skilled artisan desiring to transfect a particular cell type with DNA encoding CRIF. Preferably, the promoter sequence is a mammalian promoter sequence, and more preferably, the promoter sequence is derived from human cytomegalovirus.

The vector of the invention preferably comprises the promoter sequence described above, and also comprises suitable additional DNA sequences which may enhance transcription of DNA encoding CRIF, which may render mRNA encoding CRIF more stable, and which may even enhance translation of mRNA encoding CRIF. The vector of the invention may comprise a sequence comprising CRIF, or may comprise modifications of that sequence, which modifications specify a CRIF having enhanced properties when compared with wild type or native CRIF. Modification of DNA using recombinant DNA technology is common in the art and is described for example, in Sambrook et al. (1989, Molecular Cloning: A Laboratory Manual, Cold Spring Harbor, N.Y.).

The vector of the invention may comprise any mammalian CRIF DNA sequence. Preferably, the vector of the invention comprises rat, human or mouse CRIF DNA. More preferably, the vector of the invention comprises human CRIF DNA. Preferably, the vector of the invention is pcDNA3(4.5 Kb)-hTRH, or the vector of the invention is PCMV-TRH.

Even more preferably, the vector comprises a minigene having a promoter/regulatory sequence capable of driving CRIF expression, a 5' leader sequence comprising a prepro-TRH leader sequence, a CRIF coding region and translational stop codons, and a 3' sequence being a preproTRH 3' sequence.

Most preferably, when rat CRIF is used, the vector comprises a minigene having a total of 227 base pairs having an 18 base pair multiple cloning restriction enzyme site positioned 5' to a 50 base pair 5' region of a preproTRH gene (wherein the first base pair is at position +1 of the prepro-TRH sequence), which is positioned 5' to 24 base pairs of preproTRH signal sequence, which is positioned 5' to 66 base pairs of CRIF coding sequence, which is positioned 5' to 9 base pairs of a translational stop codon, which is positioned 5' to an 18 base pair multiple cloning restriction enzyme sequence.

By the term "vector" as used herein, is meant a DNA sequence having DNA which specifies replication and/or expression of a gene encoded thereby in a cell into which the DNA sequence is introduced. Preferably, the vector is a plasmid; however, the vector may also be a cosmid, a bacteriophage, an animal, plant or insect virus vector, or any combination thereof.

CRIF or agonists and antagonists thereof, can be used to treat a variety of disorders in humans. CRIF may be used to modulate hypothalamic pituitary adrenal (HPA) activity in the brain, the pituitary and/or the immune system. Increases in HPA activity are defined by increased hypothalamic CRF and/or increased pituitary ACTH and/or increased adrenocortical glucocorticoid production. Illness associated with hypercortisolemia such as Cushing's disease, anxiety disorders, anorexia nervosa, depression, obesity, and withdrawal from alcohol or drug dependence, may be treated with CRIF in order to reduce ACTH levels. Regarding depression, hypercortisolemia is believed to contribute to the etiology of depression and therefore, CRIF may be useful for treatment of depression. CRIF may even be used to control appetite.

CRIF may also be used to reduce ACTH and cortisol levels for treatment of chronic stress-related syndromes and symptoms including those exacerbated by stress-induced immunosuppression, such as viral infections. CRIF may be used in some cancers (those where an enhanced autoimmune response reduces the severity of the disease), and may increase the efficacy of immunity to vaccines. Anti-CRIF antibodies or other CRIF antagonists may be used to counteract the effects of CRIF during illness and may therefore be useful for treatment of hypocortisolism, isolated ACTH deficiency and premenstrual syndrome. CRIF antibodies or antagonists may also be used to systemically treat illnesses with an inflammatory component, such as colitis, and autoimmune diseases such as arthritis, conditions in which higher levels of endogenous glucocorticoids are advantageous.

Inflammatory diseases which are treatable according to the methods and compositions of the invention include, but are not limited to, diseases which are characterized as having an acute inflammatory immune response component, as those which are characterized as having irregular or periodic episodes of acute inflammatory immune responses components and as those which are termed "autoimmune" as commonly used in the art. Typically, such autoimmune diseases include systemic autoimmune diseases such as systemic lupus erythematosus, multiple sclerosis and rheumatoid arthritis. Examples of these and other inflammatory diseases may be found in any common immunology textbook, for example, in Stites et al., 1984, Basic and CLinical Immunology, $5^{th}$ Edition, Lange.

CRIF itself can be used locally to ameliorate inflammation as it is known that CRF is released locally at sites of inflammation wherein it appears to act as an autocrine or paracrine inflammatory cytokine (Karalis et al., 1991, Science 254:421). Since local CRF induces synthesis of POMC in lymphocytes, the actual mediators of these inflammatory responses may be POMC-related peptides. Thus, inhibition of the local production of POMC peptides by locally administered CRIF should ameliorate inflammatory autoimmune disease.

The current treatment of choice in ACTH disorders involves the use of glucocorticoids. Since most cells contain glucocorticoid receptors, this type of treatment induces significant side effects. In contrast, treatment using CRIF is expected to be associated with minimal overall side effects since CRIF acts specifically upon ACTH synthesizing and ACTH secreting cells. In fact, as the data provided herein establish, rats treated in vivo with CRIF exhibit no discernible deleterious side effects associated with CRIF administration.

Protocols for treatment of mammals with a CRIF disorder involving administration of an agonist or antagonist, or of CRIF itself, will be apparent to those skilled in the art and will vary depending upon the type of disease the type and age of the mammal. Treatment regimes which are contemplated include a single dose or dosage which is administered hourly, daily, weekly or monthly, or yearly. Dosages may vary from 1 μg to 1000 mg/kg of body weight of the agonist or antagonist, or of CRIF and will be in a form suitable for delivery of the compound. The route of administration may also vary depending upon the disorder to be treated.

The invention contemplates administration of CRIF to humans for the dual purpose of either treating or diagnosing a human having a CRIF disorder. The protocol which is described below for administration of CRIF to a human is provided as an example of how to administer CRIF to a human. This protocol should not be construed as being the only protocol which can be used, but rather, should be construed merely as an example of the same. Other protocols will become apparent to those skilled in the art when in possession of the instant invention. Essentially, for administration to humans, CRIF is dissolved in about 1 ml of saline and doses of 1 μg, 10 μg and 100 μg per kg of body weight are administered intravenously at 48 hour intervals. Cardiovascular and neuroendocrine function are monitored throughout the administration period.

The agonist, antagonist or CRIF is prepared for administration by being suspended or dissolved in a pharmaceutically acceptable carrier such as saline, salts solution or other formulations apparent to those skilled in such administration. The compositions of the invention may be administered to a mammal in one of the traditional modes (e.g., orally, parenterally, transdermally or transmucosally), in a sustained release formulation using a biodegradable biocompatible polymer, or by on-site delivery using micelles, gels and liposomes, or rectally (e.g., by suppository or enema) or nasally (e.g., by nasal spray). The appropriate pharmaceutically acceptable carrier will be evident to those skilled in the art and will depend in large part upon the route of administration.

Agonists or antagonists of CRIF include, but are not limited to, antibody to CRIF, a nucleic acid sequence complementary to DNA encoding CRIF, and even peptidometics. Peptidometics having CRIF-like activity include compounds which have a sufficient CRIF-like activity such that their effects on the disease being treated are beneficial to the individual being treated, which beneficial effects are similar to that of CRIF. Peptidometics may also have additional advantages over CRIF in that they may be designed such that they are capable of accessing targets which are normally relatively inaccessible to CRIF. For example, as described herein, CRIF, when administered directly into the brain of an animal, has a beneficial effect on the behavior of that animal.

However, since CRIF is a peptide, it is expected that the amount of unmodified CRIF which eventually reaches the brain following intravenous administration of CRIF to an animal will be minimal. The peripheral administration to the animal of a peptidometic having CRIF activity, which peptidometic is capable of crossing the blood-brain barrier, circumvents this problem.

"CRIF-like activity" as used here denotes an activity which is so similar to that of CRIF, i.e., which functions by the same mechanism as CRIF, so as to be virtually indistinguishable from CRIF. However, this term as used herein, should also be construed to encompass compounds which may operate by the same mechanism as CRIF, but which may have a higher specific activity than CRIF.

"Peripheral administration" as used herein, denotes administration of a compound to an animal by any route other than direct administration to the brain. Thus, peripheral administration includes, but is not limited to, oral, nasopharyngeal, intraperitoneal, intramuscular and intravenous administration of any of the compounds of the invention.

Similarly, peptidometics having CRIF-antagonist-like or CRIF-agonist-like activity may also be designed and used according to the methods of the present invention. Such CRIF-antagonist and agonist peptidometics may be administered to the animal by any peripheral route in order that they eventually reach the target area in the animal wherein they exert their effects. Additional information describing administration of peptidometics is provided in PCT/US93/01201 and U.S. Pat. No. 5,334,702, which are hereby incorporated herein by reference. Any of the techniques described in either of these two references may be employed in the present invention for the administration of peptidometics.

Peptidometics may be generated using techniques described in PCT/US93/01201 and in U.S. Pat. No. 5,334,702. Generation of anti-CRIF antibodies is described below. Nucleic acid sequence complementary to CRIF may be generated using the sequence of CRIF provided herein. Administration of antisense oligonucleotides to mammals is now common in the art and may be accomplished by using any of the administration techniques described herein.

Preferably, the CRIF of the invention is administered at a dose of 1 μg to 10 mg/kg body weight and the CRIF agonist or antagonist is administered at a dose of 1 μg to 100 mg/kg of body weight.

Compounds having CRIF, CRIF antagonist or agonist activity or which have CRIF-like activity also include compounds which are formulated so as to target specific types of cells. For example, it is now known in the art to encapsulate or otherwise formulate compounds such that they a directed to specific receptors on cells. Such formulations include antibody-tagging formulations, receptor-ligand binding formulations and the like.

The invention also includes a method of treating an inflammatory disease in a human by increasing the level of endogenous glucocorticoids in the human. The method comprises administering a CRIF antagonist to the human. Preferably, the CRIF antagonist is anti-CRIF antibody. One or more CRIF antagonists may be administered to the human either alone, or in combination with the thyroid hormones, $T_3$ or $T_4$. The thyroid hormones are administered by any convenient route, including orally, parenterally, transdermally, transmucosally, or rectally or nasally. The amount of CRIF antagonist to be administered and the amount of thyroid hormone to be administered if so desired, will be apparent to one of skill in the art of inflammatory disease. Preferably, the thyroid hormone is administered as described herein for either $T_3$ or $T_4$, and the CRIF antagonist is administered at a dose of 1 μg to 100 mg/kg of body weight daily.

It is also apparent from the data described herein that thyroid hormones may be administered to the animal without the added administration of a CRIF antagonist, for the purpose of modulating inflammatory diseases. In view of the effect of the thyroid hormones $T_3$ and $T_4$ on CRIF as demonstrated herein, thyroid hormones themselves are useful as therapeutic compounds for treatment of CRIF-related disorders. In particular, in view of the data provided herein, the thyroid hormones, $T_3$ or $T_4$, may be administered to the animal to reduce or ablate inflammatory disease.

$T_3$ or $T_4$ may be administered to the animal in an unmodified form, or in a form designed to increase the stability and/or the specific activity of $T_3$ or $T_4$ in the animal. Such modifications include those described herein with respect to CRIF. In addition to modifications of $T_3$ or $T_4$, compounds having $T_3$ or $T_4$ activity may also be generated using the technology described herein.

$T_3$ or $T_4$, modified $T_3$ or $T_4$, or a compound having $T_3$- or $T_4$-like activity, may be formulated in any of the formulations described herein with respect to CRIF. Typically, $T_3$ modified $T_3$, or a compound having $T_3$-like activity, is administered to the animal in a dose of about 10 μg to about 150 μg per adult human. Preferably, $T_3$ modified $T_3$, or a compound having $T_3$-like activity, is administered to the animal in a dose of about 15 μg to about 100 μg per adult human, and even more preferably, the dose is in the range of about 25 μg to about 75 μg per adult human.

$T_4$, modified $T_4$, or a compound having $T_4$-like activity, is typically administered to the animal in a dose of about 0.05 mg to about 0.8 mg per adult human. Preferably, $T_4$, modified $T_4$, or a compound having $T_4$-like activity, is administered to the animal in a dose of about 0.075 mg to about 0.6 mg per adult human, and even more preferably, the dose is in the range of about 0.1 mg to about 0.4 mg per adult human.

By "$T_3$-like activity" or by "$T_4$-like activity" as used herein, is meant compounds which have an activity which is so similar to that of either of $T_3$ or $T_4$, respectively, i.e., which functions by the same mechanism as $T_3$ or $T_4$, so as to be virtually indistinguishable from either of $T_3$ or $T_4$, respectively. However, this term as used herein, should also be construed to encompass compounds which may operate by the same mechanism as either of $T_3$ or $T_4$, but which may have a higher specific activity than either of $T_3$ or $T_4$.

Compounds having $T_3$- or $T_4$-like activity also include compounds which are formulated so as to target specific types of cells. For example, it is now known in the art to encapsulate or otherwise formulate compounds such that they a directed to specific receptors on cells. Such formulations include antibody-tagging formulations, receptor-ligand binding formulations and the like.

$T_3$, $T_4$, modified $T_3$ or $T_4$, or compounds having $T_3$- or $T_4$-like activity may be prepared for administration by being suspended or dissolved in a pharmaceutically acceptable carrier such as saline, salts solution or other formulations apparent to those skilled in such administration. The compositions of the invention may be administered to a mammal in one of the traditional modes (e.g., orally, parenterally, transdermally or transmucosally), in a sustained release formulation using a biodegradable biocompatible polymer, or by on-site delivery using micelles, gels and liposomes, or rectally (e.g., by suppository or enema) or nasally (e.g., by nasal spray). The appropriate pharmaceutically acceptable carrier will be evident to those skilled in the art and will depend in large part upon the route of administration.

In addition to treatment of disease using CRIF or agonists or antagonists thereof, anti-CRIF antibody may be used to diagnose CRIF-related diseases in mammals suspected of having such diseases. For example, samples of blood may be obtained from mammals suspected of having a CRIF-related disease or from normal individuals. Antibody is added to each blood sample and the amount of CRIF in the sample bound to the antibody is measured using ordinary antibody measuring techniques such as Enzyme Linked Immunoabsorbant Assay (ELISA) or Radioimmunoassay (RIA). A higher or lower amount of antibody bound to the CRIF in the mammal's blood compared with normal blood is an indication that the mammal has a CRIF-related disease. These types of diagnostic tests are well known in the art and are used for measurement of serum levels of other hormones such as ACTH, cortisol or even TRH.

Anti-CRIF antibodies immueasily generated by immunization of an animal with the CRIF peptide identified herein. Protocols for the generation of antibodies (either monoclonal or polyclonal antibodies) to a known peptide are described in Harlow et al. (1988, In: Antibodies, A Laboratory Manual, Cold Spring Harbor, N.Y.), which protocols can be easily followed by the skilled artisan. Polyclonal antibodies to CRIF may be raised in any suitable animal, such as a mouse or a rabbit. Monoclonal anti-CRIF antibodies are generated by immunization of a mouse with CRIF peptide followed by production of hybridoma cells capable of secreting anti-CRIF antibody.

Diagnostic tests for the identification of CRIF-related disease states are not limited to the use of anti-CRIF antibody. Other tests may also be used including nucleic acid based tests such as hybridization and/or polymerase chain reaction (PCR) assays. In this instance, samples of cells or tissue are obtained from blood (lymphocytes, platelets), the pituitary or the placenta or amniotic fluid of normal healthy mammals or mammals suspected of having a CRIF-related disease, which samples are processed for hybridization or PCR assays following ordinary protocols described for example, in Sambrook et al. (1989, Molecular Cloning: A Laboratory Manual, Cold Spring Harbor, N.Y.). Probes and primers which can be used in these assays include nucleic acid sequences comprising CRIF, which sequences are described herein.

An additional diagnostic test may be used which test takes advantage of the ability of CRIF to affect levels of ACTH. In this test, a bolus dose of CRIF (1 μg–1000 mg/kg body weight) is administered to a mammal suspected of having a CRIF disorder. Plasma levels of ACTH and cortisol are then measured in the mammal. In cases where CRIF is under-produced in the mammal, levels of ACTH will be more suppressed compared with those in a normal mammal. In cases where CRIF is overproduced, levels of ACTH will be less suppressed than those in a normal mammal. Thus, this test is a measure of under or over production of CRIF as assessed by the level of ACTH in a mammal. This test may be useful in situations wherein direct measurement of CRIF proves difficult.

There are two general animal models which may be used to test the efficacy of CRIF in some of the diseases described herein. In the first model, hypersecretion of ACTH, generation of ulcers and depressive behavior can be examined. In this model the Wistar-Kyoto (WKY) rat, which exhibits hypersecretion of ACTH and enhanced synthesis of anterior pituitary ACTH, is used. Hypersecretion of ACTH and enhanced synthesis of anterior pituitary ACTH is measured by measuring levels of POMC mRNA, which in this case are increased compared with other rat strains (Redei et al., 1994, Am. J. Physiol. 266:R353–R360). The WKY rat also exhibits increased vulnerability to stress ulcer and spontaneous depressive behavior as measured in different paradigms including the Porsolt swim test, a test used for screening of anti-depressant agents (Pare and Redei, 1993, J. Physiol. 87:229–238).

To test the efficacy of CRIF, WKY rats are pretreated with intravenous injection of CRIF suspended in saline at a concentration of 1–10 μg/kg of body weight. Struggling time and floating time of treated animals is compared with that exhibited by control animals administered saline alone. Increased struggling time and decreased floating time during the length of the test (15 minutes) is expected if CRIF acts as an anti-depressant. To determine the effect of CRIF on acquisition of stress ulcers, animals are treated as described above, exposed to water restraint and the number of ulcers in treated versus untreated rats is measured (Pare and Redei, 1993, J. Physiol. 87:229–238). It is expected that CRIF treated WKY rats will have fewer ulcers than their untreated counterparts.

In the second animal model, the female Lewis rat, which rat exhibits increased susceptibility to autoimmune illness, is used (Sternberg et al., 1989, Proc. Natl. Acad. Sci. U.S.A. 86:2374–2378). This increased susceptibility seems to correlate with an inability to mount an appropriate glucocorticoid response to an inflammatory agent. When these animals are either stressed or are treated with glucocorticoids, their autoimmune condition improves suggesting that their low levels of ACTH and glucocorticoids are responsible for their increased vulnerability to autoimmune illness.

To perform this second test, female Lewis rats are pretreated with CRIF antibody and their ability to mount an enhanced ACTH and glucocorticoid response to an inflammatory agent is assessed and compared with that response exhibited by untreated animals.

A frequently used animal inflammatory response model involves induction of arthritis by systemic injection of a streptococcal cell wall (SCW) preparation. In this model, the animals become arthritic following injection of the cell wall preparation. To examine the effect of CRIF in this model, female Lewis rats are implanted with osmotic minipumps that are designed to deliver a continuous intravenous flow of CRIF antibody approximately one week prior to administration of the SCW preparation. Administration of CRIF antibody is expected to increase ACTH levels and consequently glucocorticoid levels, thus rendering Lewis rats less susceptible to arthritis. Sprague-Dawley rats which do not exhibit increased susceptibility to autoimmune illness may be used as a control.

CRIF is also useful for treatment of diseases associated with increased prolactin secretion since, as described herein, CRIF inhibits secretion of prolactin. Prolactin, which plays a major role in milk production in animals, is a large peptide which is produced by the anterior pituitary by lactotrophs, somatotrophs and by cells in the placenta. Somatotrophs also produce growth hormone and in fact, prolactin is a member of the same peptide family as growth hormone peptide. Receptors for human prolactin have been cloned. Such receptors are found in T cells, B cells, cells of the testes and ovaries, and large amounts of prolactin receptors are found in mammary glands. Secretion of prolactin is induced by stress and by suckling. Further, there is evidence that the effect of prolactin on cells occurs via a negative type of regulation. Prolactin is reviewed in DeGroot. 1989, Endocrinology, W.B. Saunders Co.

The ability of CRIF to inhibit prolactin secretion is clinically important. For example, hyperprolactonemia can lead to amenorrhea/galactorrhea and gynecomastia in humans. Further, hyperprolactinemia in human males is associated with a decrease in libido and potency and in some cases hypogonadism. In addition, chronic anovulation in women is attributed to prolactin hypersecretion (Palermo et al., 1994, "Chronic anovulation due to prolactin hypersecretion" Acta Europaea Fertilitatis 25(3): 161–172). All of these symptoms are reversed by reducing prolactin levels (DeGroot. 1989, Endocrinology, W.B. Saunders Co.).

Prolactin also plays a role in immune function, by increasing the immune responsiveness of T cells and other immune cells. For example, some T cells require prolactin for proliferation (Prystowsky et al., 1994, Immunomethods 5(1): 49–55). Further, prolactin is known to play a role in autoimmune diseases such as systemic lupus erythematosus (Walker et al., 1995, "Epidemiology of rheumatoid arthritis" Lupus 4(1): 3–9) and rheumatoid arthritis (Silman, 1994, APMIS 102(10): 721–728).

In addition to the above, prolactin is an important component in breast cancer and other tumors having prolactin receptors. In at least the latter instance, prolactin plays a role in stimulating the growth of cells. Thus, inhibition of prolactin secretion using CRIF provides a means of cells growth inhibition and therefore tumor growth inhibition (Zumoff, 1994, "Hormonal profiles in women with breast cancer", Obstetrics & Gynecology Clinics of North America 21(4) :751–772).

Some of the endocrine consequences of hyperprolactinemia are currently treated with the dopamine receptor agonist bromocriptine mesylate (Parlodel™, Sandoz). According to the present invention, treatment of individuals with CRIF provides yet another therapeutic paradigm for prolactin-associated disorders. Prolactin-associated disorders therefore include, but are not limited to hyperprolactonemia-associated diseases including amenorrhea/galactorrhea and gynecomastia, decreased in libido and potency, hypogonadism, chronic anovulation, immune disorders including autoimmune diseases such as systemic lupus erythematosus and rheumatoid arthritis, and breast cancer and other tumors having prolactin receptors.

CRIF is also useful for treatment of behavioral disorders in animals and humans. As the data provided herein establish, CRIF has marked effects on the behavior of animals administered this peptide. The behavioral responses following icv administration indicate that CRIF has neurobehavioral effects in addition to its regulatory role in anterior pituitary ACTH and prolactin release. The results of the experiments described herein suggest that CRIF possesses arousal and anxiolytic properties. The data further suggest that the observed neuroendocrine and behavioral response in rats administered CRIF may be activated simultaneously by independent mechanisms.

CRIF, or a peptidometic having CRIF-like activity, may be useful for treatment of behavioral symptoms associated with anxiety disorders. Such anxiety disorders include, but are not limited to generalized anxiety disorder, panic disorder, obsessive-compulsive disorder and post-traumatic stress disorder (American Psychiatric Association: Diagnostic and Statistical Manual of Mental Disorders: DSM-IV, Washington, D.C. American Psychiatric Association, 1994).

The present invention also includes a CRIF receptor protein. Such a receptor may be isolated in an ordinary receptor-binding assay using radiolabelled CRIF which retains biological activity. As is apparent from the experimental data presented herein, tyrosine-CRIF is bioactive in AtT20 cells. Thus, tyrosine-CRIF which is radioalabelled with iodinated tyrosine is predicted to be biologically active in AtT20 cells. Thus, $^{125}$I-Tyrosine-CRIF may be added to AtT20 or similar cells in a standard receptor binding assay for isolation of the CRIF receptor protein. Once the CRIF receptor protein is isolated, a partial peptide sequence is obtained from which a DNA probe is generated, which probe may be used in a hybridization assay to identify and subsequently isolate DNA encoding CRIF receptor protein. CRIF receptor protein so isolated, is useful for further identification of compounds which bind CRIF receptor and for the identification and generation of compounds which have therapeutic value for treatment of CRIF-related diseases.

Experimental Data

The experiments described below establish the identity and function of the CRIF of the invention. The experiments are not to be considered as limiting the scope of the appended claims.

It has now been discovered that CRIF is comprised of a peptide which is a component of the hypothalamic prepro-thyrotropin-releasing hormone (prepro-TRH) in that it is present within one of the TRH intervening sequences. This discovery was based upon the observation that prepro-TRH, but not the mature TRH tripeptide, is capable of inhibiting both basal and stress- or CRF-induced ACTH synthesis and secretion. The only pathophysiologically meaningful condition in which both basal and stress-induced ACTH levels are suppressed is in the hypothyroid state. In this state, elevated levels of hypothalamic prepro-TRH are observed, yet mature TRH does affect ACTH secretion (Segerson et al., Science 238:78, 1987). Rat pro-TRH comprises 255 amino acids and contains 5 copies of the TRH tripeptide plus seven intervening sequences (Lechan et al., 1986, Science, 231:159–161). In the experiments described herein, a cDNA encoding prepro-TRH was transfected into AtT-20 cells, a mouse pituitary tumor cell line which expresses and processes POMC, the precursor of ACTH, and which cell line processes prepro-TRH (Sevarino et al., 1989, J. Biol. Chem. 264:215229–215235; Nillni et al., 1993, Endocrinology 132:1260–1270). Transient transfection with prepro-TRH results in inhibition, in a dose response manner, of both synthesis and secretion of ACTH under unstimulated and CRF-stimulated conditions.

Cell cultures. AtT-20 cells (Sabol, 1980, Arch. Biochem. Biophys. 203:37–48) were maintained and subcultured in DMEM supplemented with 10% fetal calf serum plus antibiotics in a humidified 10% $CO_2$ atmosphere. In the experiments described herein, the cells were incubated in steroid-free (charcoal-stripped) fetal calf serum (FCS).

Extraction and Chromatography of CRIF. Hypothalamic extracts from adult male Wistar and WKY rats were prepared as described by Redei et al. (In: Neuropeptides and Stress, Eds. Tache et al., Hans Selye Symposia on Neuroendocrinology and Stress, 1989, Springer-Verlag, New York). Briefly, 10 hypothalami each were suspended in water containing 0.1% ascorbic acid and 200 KIU/ml aprotinin (Sigma). The suspension was centrifuged at 10,000×g at 4° C. for 30 min. Supernatants were filtered through a Sephadex G-50 (fine) column at a flow rate of 0.25 ml/min using 50% acetic acid as eluent. Two minute fractions were collected and evaporated to dryness in a Speed-Vac concentrator (Savant System Inc.,). Fractions were bioassayed using AtT-20 cells in the CRIF assay. Those fractions exhibiting CRIF activity were collected and stored until further experimentation.

Plasmids. The expression vector pCMV-TRH comprises cDNA encoding rat TRH under the control of the human cytomegalovirus (HCMV) immediate early promoter (Lee et al., 1988, J. Biol. Chem. 263:16604–16609). To generate this vector, a 1,322 bp fragment comprising sequences encoding TRH was excised from the plasmid pSP64, by digestion with HindIII and EcoRI. This fragment was then inserted into pcDNA-3 (Invitrogen, San Diego, Calif.) to generate pCMV-TRH comprising the HCMV immediate early promoter, the bovine growth hormone polyadenylation signal and cDNA encoding TRH inserted therebetween. This plasmid also contains sequences encoding resistance to neomycin and can therefore be used to select stably transfected cells. The structure of the rat prepro-TRH molecule is presented in FIG. 1.

Referring to FIG. 1, two deletions were made in the expression vector PCMV-TRH. The first deletion, ΔBstEII, contains a deletion between nucleotides 506 and 787 in TRH cDNA. This results in deletion of amino acids 117 to 229 of prepro-TRH. To generate ΔBstEII, pCMV-TRH was digested with BstEII, and a 6.4 kb fragment was isolated therefrom. The 5' sticky ends were filled in with Klenow to create blunt ends, and the 6.4 kb fragment was then religated to form ΔBstEII. This religation results in restoration of the original wild type reading frame. The second deletion, ΔApaI, contains a deletion from nucleotides 746 in the prepro-TRH molecule to the ApaI site in the pcDNA-3 vector immediately downstream from the prepro-TRH cDNA insert (i.e., in the multiple cloning site). This results in a deletion extending from amino acid 216 to the carboxyl terminal end of prepro-TRH. To generate this deletion, pCMV-TRH was digested with ApaI, and a 6.1 kb fragment was isolated therefrom. This fragment was religated to form ΔApaI.

Transfection of cells. AtT-20 cells were transiently transfected (using Lipofectin) with 0–10 μg of pCMV-TRH, ΔBstEII or ΔApaI, and an amount of pcDNA-3 such that the total amount of transfected DNA was always 10 μg. Plasmid DNA in 1 ml of OPTI-MEM (Gibco/BRL) was mixed with 20 μg of Lipofectin reagent (Gibco/BRL) in 1 ml OPTI-MEM and the mixture was incubated for 15 minutes at room temperature. AtT-20 cells, seeded at a density of 1×10$^5$ cells/well in 35 mm six-well plates, were incubated for 24 hours in DMEM containing 10% steroid-free FCS to approximately 60% confluency. Cells were washed once with OPTI-MEM and then overlaid with the transfection mixture. Incubation was continued for 6 hours at 37° C. The transfection mixture was removed and DMEM containing 10% steroid-free fetal calf serum was added to the cells which were further incubated for 18 hours at 37° C. in the presence or absence of 10 nM CRF. At the end of the incubation period, the supernatant was removed from the cells, clarified by centrifugation at 1000 g and 4° C. and then stored at −80° C. Total RNA was also isolated from each well.

For stable transfection, AtT-20 cells were plated at 2×10$^5$ cells/100 mm dish and incubated for 24 hours (approximately 40% confluency). Cells were transfected as described above with 10 μg pCMV-TRH DNA in 2 ml OPTI-MEM and 40 μg of Lipofectin Reagent in 2 ml OPTI-MEM. The transfection mix was replaced after 6 hours with DMEM plus 10% FCS. After 48 hours, the cells were trypsinized and split at a 1:6 ratio, and after a further 72 hours stably transfected cells were selected in the presence of 200 µg/ml G-418 (Gibco/BRL). After three weeks incubation in G-418, individual colonies of resistant cells were isolated and maintained in the presence of G-418.

Calcium phosphate transfection of primary anterior pituitary cells. Cells were seeded at $2\times10^5$ cells/well in 24-well plates (1 ml/well), and incubated for 48 hours in DMEM plus 10% steroid-free FCS. Fresh medium was added 3 hours prior to transfection. Cells were transiently transfected using the Gibco/BRL calcium phosphate transfection system. Each well received 0.5 ml of a $CaPO_4$-DNA precipitate formed as follows: 0.25 ml of a 10 µg DNA/250 mM $CaCl_2$ solution was added dropwise to 0.25 ml of 1× Hepes-buffered saline (1× HBS=137 mM NaCl, 21 mM Hepes, pH 7.05, 0.75 mM $Na_2HPO_4$) while bubbling air through the mixture. Precipitates were then incubated at room temperature for 20 min. After rinsing the cells with DMEM, precipitates were added to the cells and incubated at 37° C. for 8 hours. The precipitates were removed from the cells, and the cells were rinsed with DMEM and incubated for 14 hours in DMEM plus 10% steroid-free FCS.

Bioassay. The bioactivity of various synthetic peptides corresponding to the various prepro-TRH intervening sequences was assessed in AtT-20 or primary anterior pituitary cells. All experiments were conducted in triplicate. To perform this assay, AtT-20 cells were plated at a density of 105 cells/well in 24 well plates. After 24 hours, the medium was removed and replaced with steroid-free medium containing the test peptide at a concentration of $10^{-10}$–$10^{-6}$ M. When primary pituitary cultures were used, freshly dispersed anterior pituitary cells (1–$2\times10^5$ cells/well) were plated in 24 well plates for 48 hours using steroid free media. Again, after 24 hours, the medium was removed and replaced with steroid-free medium containing the test peptide at a concentration of $10^{-10}$–$10^{-6}$ M. The supernatants from the cells were harvested after 4 hours of incubation under unstimulated or CRF-stimulated conditions. AtT-20 cells were stimulated with 50 nM CRF and primary pituitary cells were stimulated with 10 nM CRF. The supernatants were centrifuged and stored at −80° C.

Radioimmunoassay. ACTH-like immunoreactivity was measured using an antiserum which reacts with amino acids 1–24 and 1–39 on ACTH on an equimolar basis. The assay is described in Redei et al. (1988, Endocrinology, 123:2736–2743). For these studies, $^{125}$I-ACTH 1–39 was used as a tracer. This assay is capable of detecting as little as 3 pg ACTH/tube. Intraassay and interassay coefficients of variation were 6.46 and 11.6% respectively.

Isolation of RNA and Northern Analysis. Cells were lysed using 0.75 ml Trizol (RNA isolation buffer; GIBCO/BRL). Chloroform (100 µl) was added to each sample and the mixture was placed on ice for 15 minutes whereupon the organic and aqueous phases were separated by centrifugation at 16,000 g for 20 minutes at 4° C. The upper aqueous phase was mixed with an equal volume of isopropanol and placed at −20° C. for 1–3 hours or overnight to precipitated the RNA. Precipitated RNA was collected by centrifugation at 16,000 g for 20 minutes at 4° C. and the pellet was washed twice with 75% ice-cold ethanol and dissolved in 10 µl of sterile distilled water. The quantity and quality of the RNA was assessed by gel electrophoresis and by spectrophotometry.

Northern blot hybridization was performed as described (Redei et al., 1993, Endocrinology, 133:452–460). Briefly, total RNA was electrophoresed, transferred to nitrocellulose filters and was fixed thereupon by UV crosslinking. Filters were prehybridized for 3–6 hours at 42° C. in prehybridization buffer and were hybridized for 16 hours at 42° C. in the presence of a $^{32}$P-labeled probe labeled by random primer labeling. The POMC probe comprises a 923 bp fragment obtained from the plasmid pMKSU16 encoding mouse POMC DNA (Uhler et al., 1983, J. Biol. CHem. 258:257–261). Since CRF is a potent stimulator of POMC biosynthesis (Plotsky, 1991, J. Neuroendrocrinol. 3:1–9), inhibition of POMC synthesis is a measure of CRIF activity. The TRH probe comprises a 1322 base pair fragment obtained from the plasmid pSP64 (Lechan et al., 1986, Science 231:159–161). Following incubation, filters were washed twice for 15 minutes each in 2× SSC/0.1% SDS at room temperature, twice for 30 minutes each in 0.1× SSC/0.1% SDS at 52° C. and were then exposed to X ray film at −80° C. using intensifying screens. These filters were subsequently stripped and reprobed under similar conditions using a $^{32}$P-labeled GAPD cDNA probe. GAPD is a housekeeping gene which is used herein as a measure of the amount of sample loaded in each well of the gel. The amount of hybridization was measured by densitometry and in each case, comparison of mRNA levels were made of RNAs on the same filter. POMC mRNA levels were normalized to the amount of GAPD mRNA in each sample.

CRIF activity in Wistar and WKY rat hypothalamic extracts. To establish that AtT-20 cells respond to CRIF, hypothalamic extracts obtained from Wistar and WKY rats were fractionated by molecular weight and the appropriately sized fractions were assayed for their ability to affect ACTH production in AtT-20 cells. Unstimulated ACTH levels produced by these cells served as a baseline index. Several fractions, (fraction numbers 32–34) exhibited a decrease in the basal level of secretion of ACTH. The inhibition of basal level ACTH secretion was significantly higher in cells treated with hypothalamic extract from Wistar rats (<40% of control levels) compared to WKY (60% of control levels).

Hypothalamic prepro-TRH mRNA levels in Wistar and WKY rat hypothalami were assessed by Northern hybridization analysis. The relative level of prepro-TRH mRNA (normalized to levels of β-actin mRNA) was higher in Wistar rats compared with WKY rats (0.178+0.02 vs. 0.117+0.03, respectively). These results establish that WKY rats, which rats hyperexpress POMC (Redei et al., 1994, Am. J. Physiol. 266:R353–R360), exhibit decreased expression of hypothalamic prepro-TRH mRNA. In addition, hypothalamic extract obtained from these rats exhibits a decreased ability to suppress ACTH secretion in AtT-20 cells. Moreover, secretion of ACTH in AtT-20 cells is decreased in response to CRIF activity.

Figure 2:
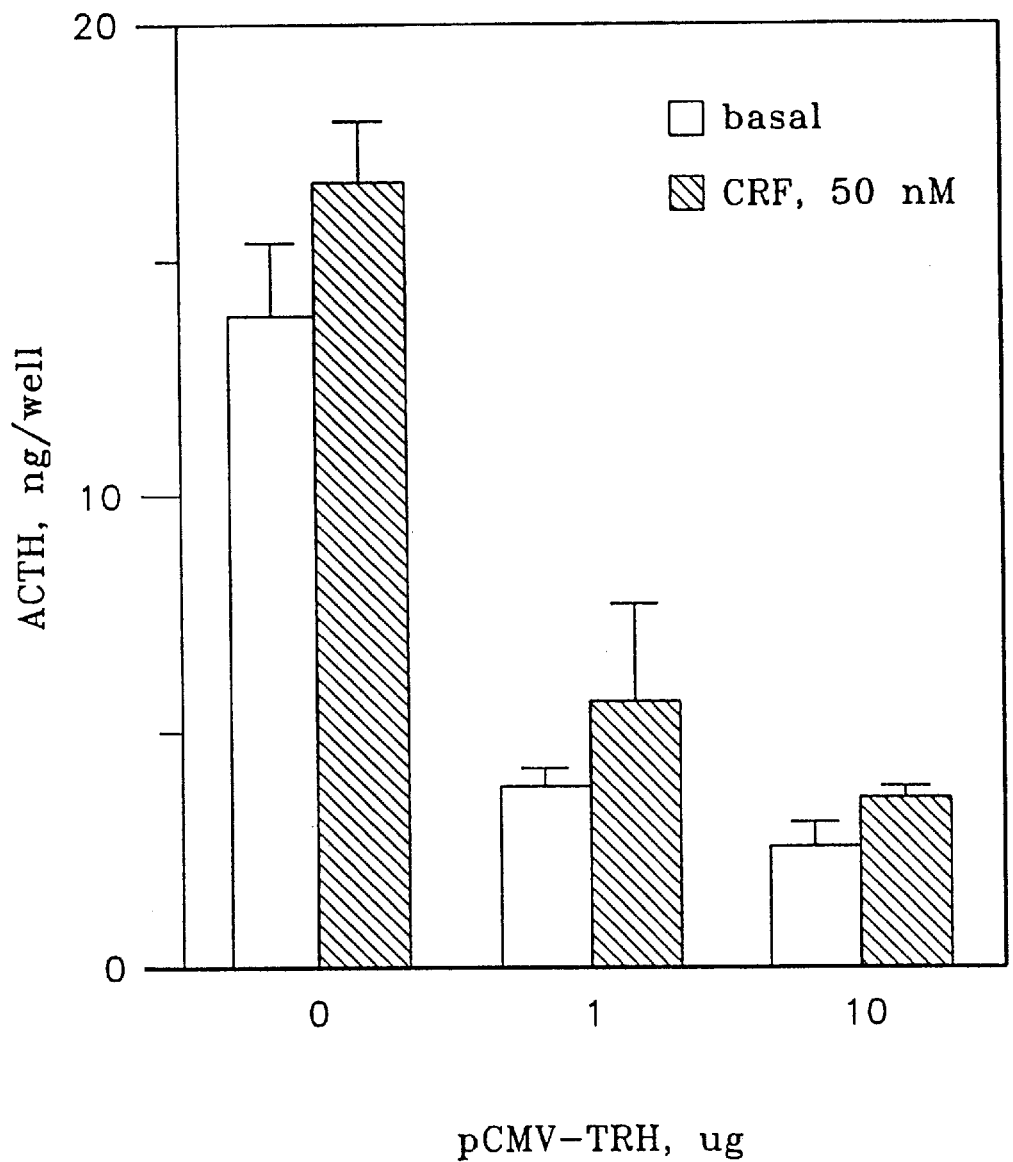
FIG. 2 is a diagram depicting basal and CRF stimulated ACTH levels in AtT-20 cells which are transfected with vector plasmid alone (0 μg) or are transfected with various concentrations of pCMV-TRH. The total amount of plasmid DNA transfected in each lane is 10 μg.

Transfection with pCMV-TRH. Unstimulated AtT-20 cells which were transiently transfected with the TRH expression vector pCMV-TRH, secreted reduced amounts of ACTH compared with cells which were not transfected. Surprisingly, even concentrations of DNA as low as 1 µg resulted in maximal inhibition of ACTH secretion (FIG. 2). CRF stimulated ACTH secretion was also inhibited in transfected cells (FIG. 2).

Figure 3:
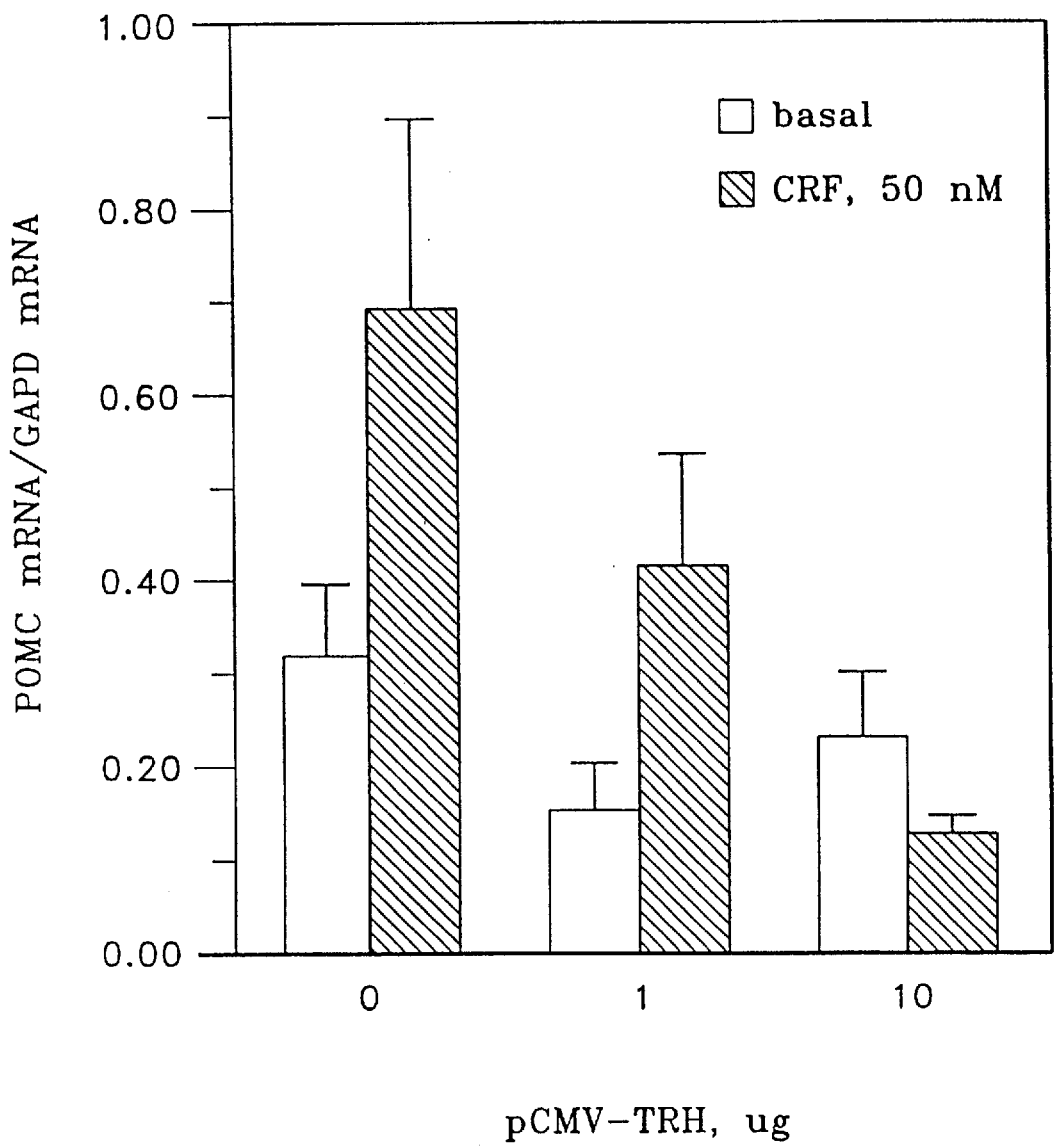
FIG. 3 is a diagram depicting the amount of POMC/GAPD (proopiomelanocortin/glyceraldehyde-3-phosphate dehydrogenase) mRNA in AtT-20 cells which are transfected with vector plasmid alone or are transfected with various concentrations of pCMV-TRH. The total amount of plasmid DNA transfected in each lane is 10 μg.

Steady state levels (either basal levels or CRF-stimulated levels) of POMC mRNA were also reduced in pCMV-TRH transfected cells as compared with untransfected control cells (FIG. 3). In yet another experiment, relative basal levels of POMC mRNA (POMC mRNA signal/GAPD mRNA signal) were 0.69+0.03 in control transfected cells, and in pCMV-TRH transfected cells these levels were suppressed in a dose-dependent manner as follows: 1 µg pCMV-TRH DNA: 0.70+0.02; 5 µg pCMV-TRH DNA: 0.52+0.05: 10 µg pCMV-TRH DNA: 0.36+0.003. CRF stimulation resulted in an increase of POMC mRNA levels to 0.82+0.04 in mock transfected cells; pCMV-TRH transfected cells exhibited somewhat reduced levels of POMC mRNA compared with the mock transfected cell level as follows: 1 μg PCMV-TRH DNA: 0.68+0.04; 5 μg pCMV-TRH DNA: 0.63+0.13 and 10 μg pCMV-TRH DNA: 0.75+0.11, respectively.

Figure 6:
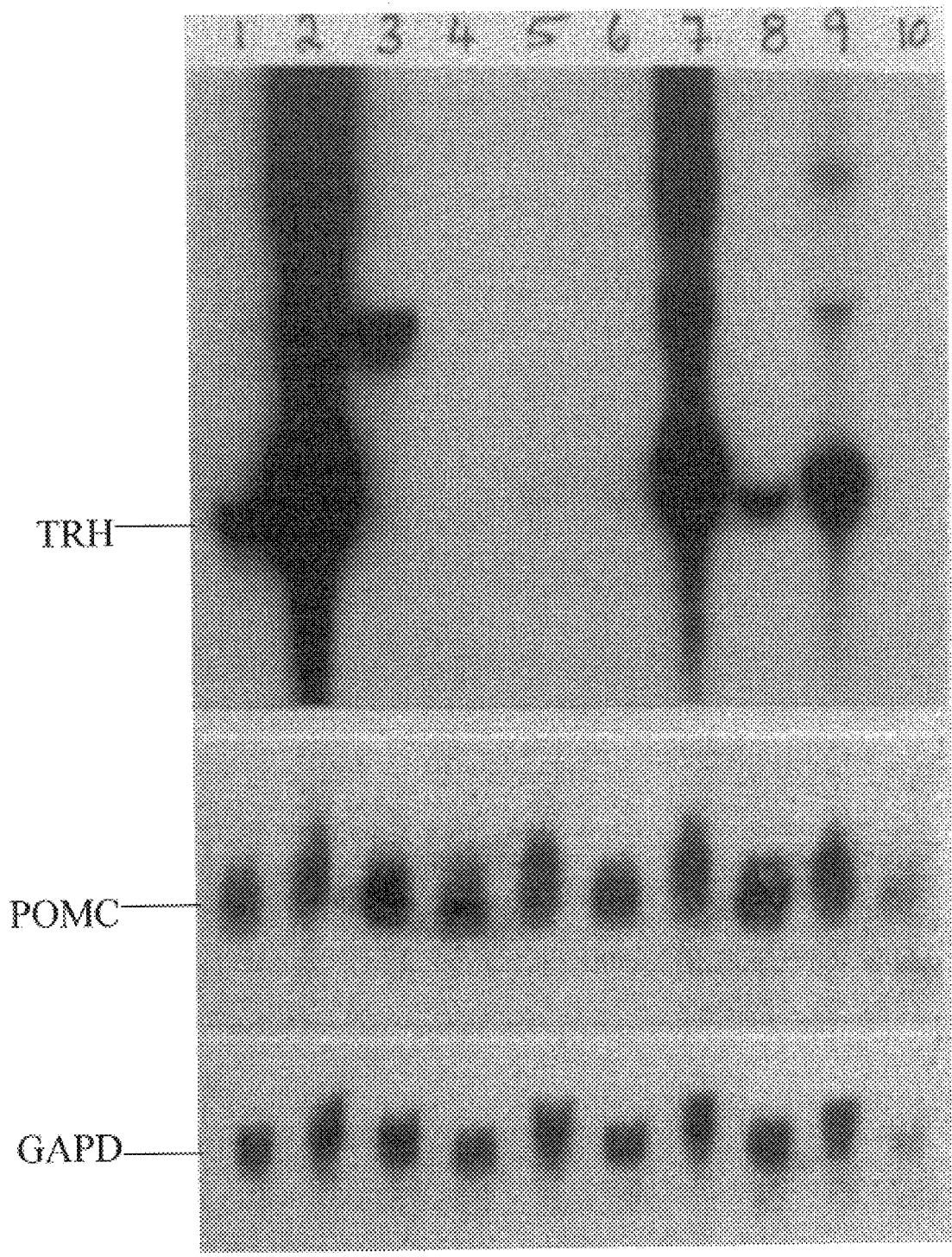
FIG. 6 is an autoradiogram depicting Northern hybridization analysis of TRH, POMC and GAPD mRNA synthesis in AtT-20 clones stably transfected with pCMV-TRH (lanes 1–9) and in untransformed AtT-20 cells (lane 10).

Clonal cell lines stably transfected with pCMV-TRH express differing levels of prepro-TRH mRNA (FIG. 6; lanes 1–9). However, irrespective of the levels of prepro-TRH mRNA, relative levels of POMC mRNA were suppressed by 50% compared with untransfected AtT-20 cells (FIG. 6; lane 10).

Figure 4A:
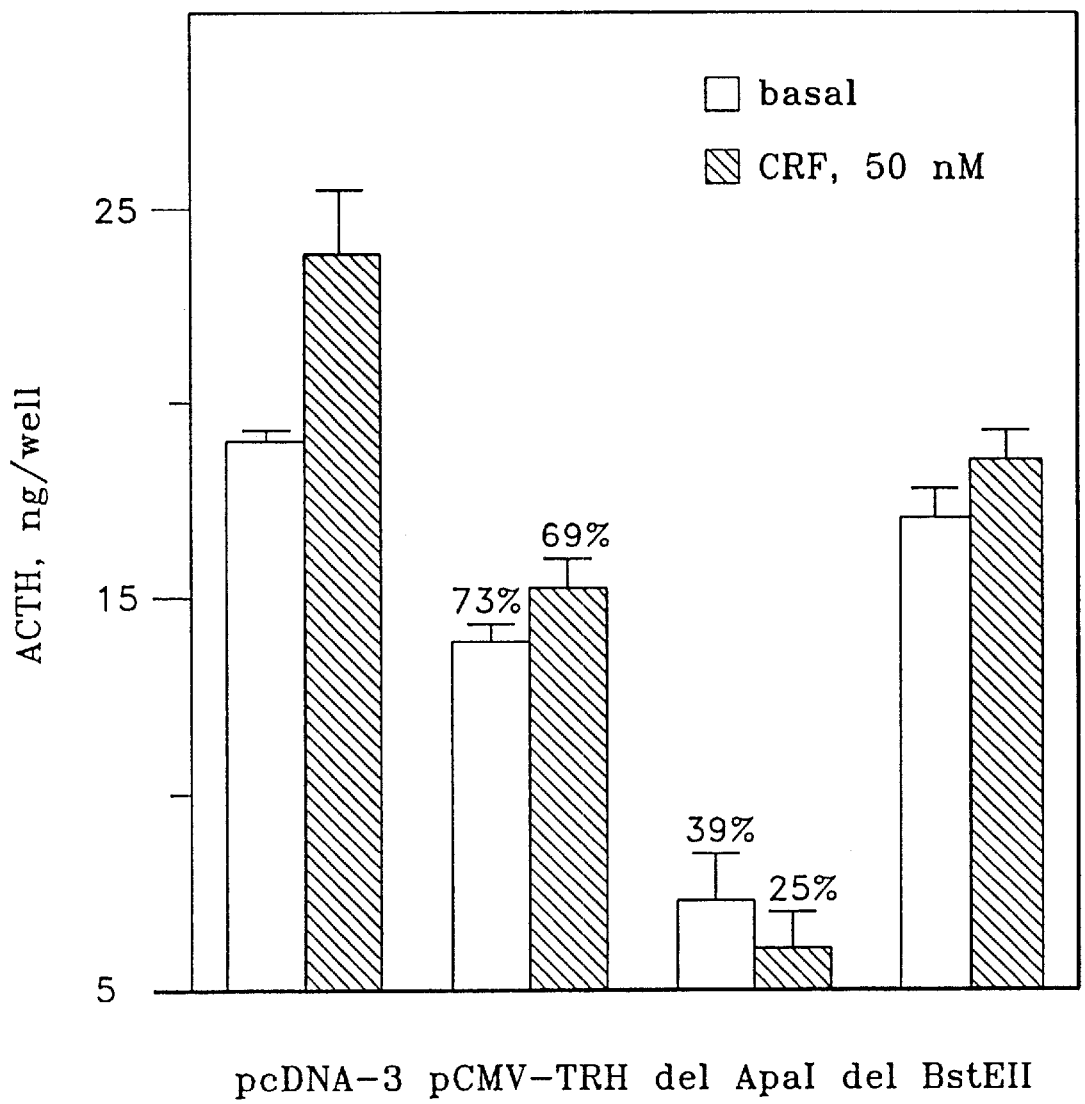
FIG. 4, comprising parts A and B, is a diagram and an autoradiogram depicting levels of ACTH and POMC produced in AtT-20 unstimulated or CRF stimulated cells which are transfected with 1 μg of vector plasmid, pcDNA3 (Invitrogen), or are transfected with 1 μg of pCMV-TRH, ΔBstEII or ΔApaI. In A, the levels of ACTH are shown. Levels of ACTH in the variously transfected cells are shown from left to right as follows: pcDNA3, pCMV-TRH, ΔBstEII, ΔApaI. In B, the amount of POMC mRNA in each type of transfected cell is shown. The control panel in this figure indicates pcDNA-transfected cells. Identical samples were loaded in each lane in each set of panels.
Figure 4B:
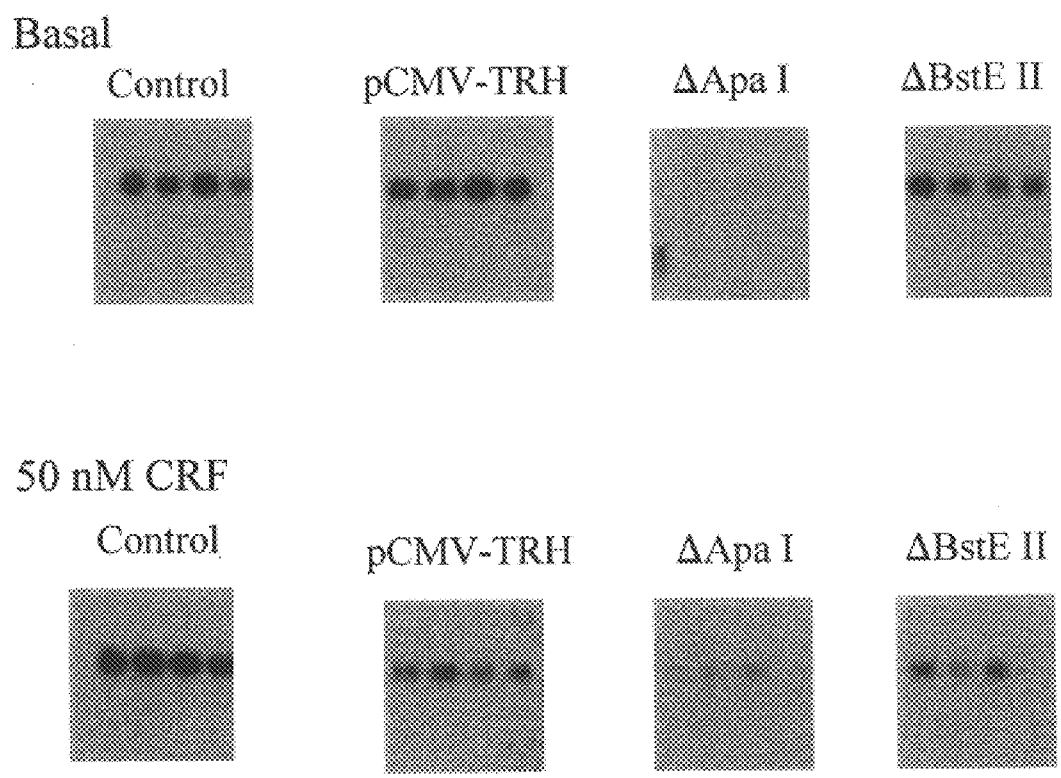

Transfection of cells with ΔBstEII and ΔApaI. When deletions were made within the prepro-TRH sequence and cells were subsequently transfected with plasmids containing these deletions, CRIF activity was found to reside within the prepro-TRH 119–215 amino acid fragment. In these experiments, unstimulated AtT-20 cells transiently transfected with 1 μg of ΔApaI exhibited decreased basal secretion of ACTH, which decrease was even more marked than that exhibited by PCMV-TRH transfected cells (FIG. 4A). In contrast, transient transfection of cells with ΔBstEII did not result in any significant decrease in basal secretion of ACTH. Furthermore, CRF stimulated ACTH secretion was reduced in cells transfected with either ΔApaI or pCMV-TRH (FIG. 4A). When levels of POMC were assessed in these cells by Northern hybridization analysis, the results were identical in that basal POMC levels were reduced in unstimulated cells transfected with ΔApaI and CRF stimulated levels of POMC were reduced in cells transfected with both ΔApaI and with pCMV-TRH (FIG. 4B).

Figure 5:
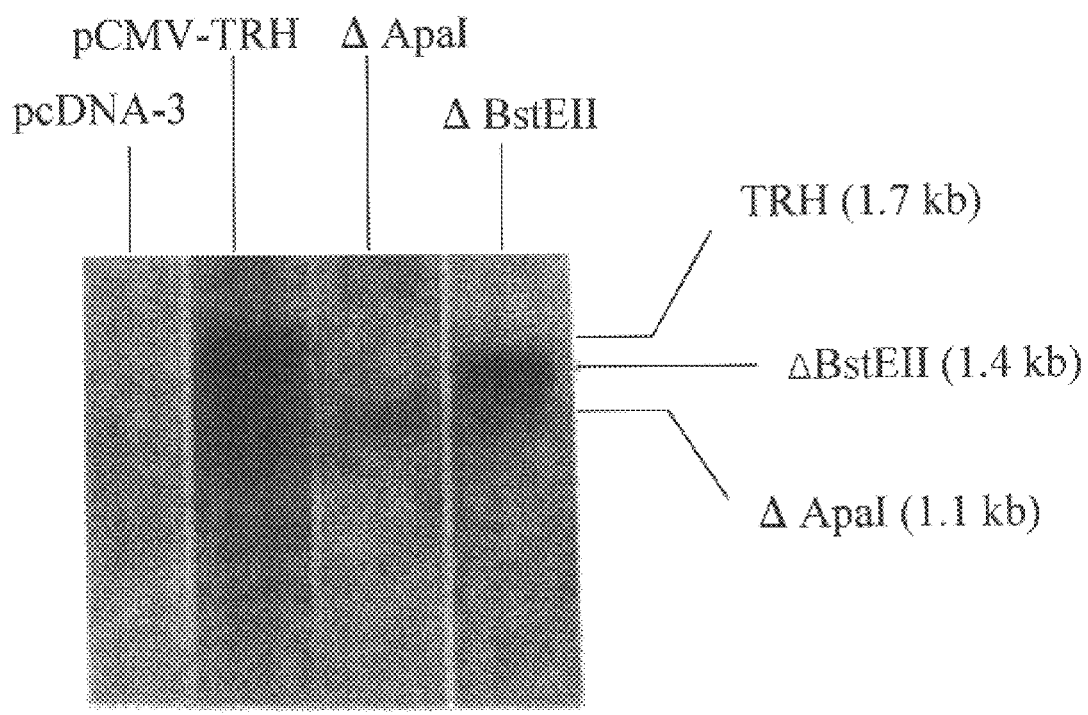
FIG. 5 is an autoradiogram depicting Northern hybridization analysis of poly $A^+$ RNA showing TRH-specific mRNA synthesized in cells transiently transfected with control, non-TRH-containing DNA (pcDNA3), or with pCMV-TRH, ΔApaI or ΔBstEII. The size of each mRNA produced is indicated at the right of the figure.

Expression of TRH specific mRNA was assessed in AtT-20 cells which were transiently transfected with either pCMV-TRH, ΔBstEII or ΔApaI. Poly A$^+$ RNA was obtained from each set of cells and was analyzed by Northern hybridization. In each instance, mRNA of the expected size was observed as follows: Full length TRH=1.7 kb; ΔBstEII= 1.4 kb; ΔApaI=1.1 kb (FIG. 5).

Figure 7:
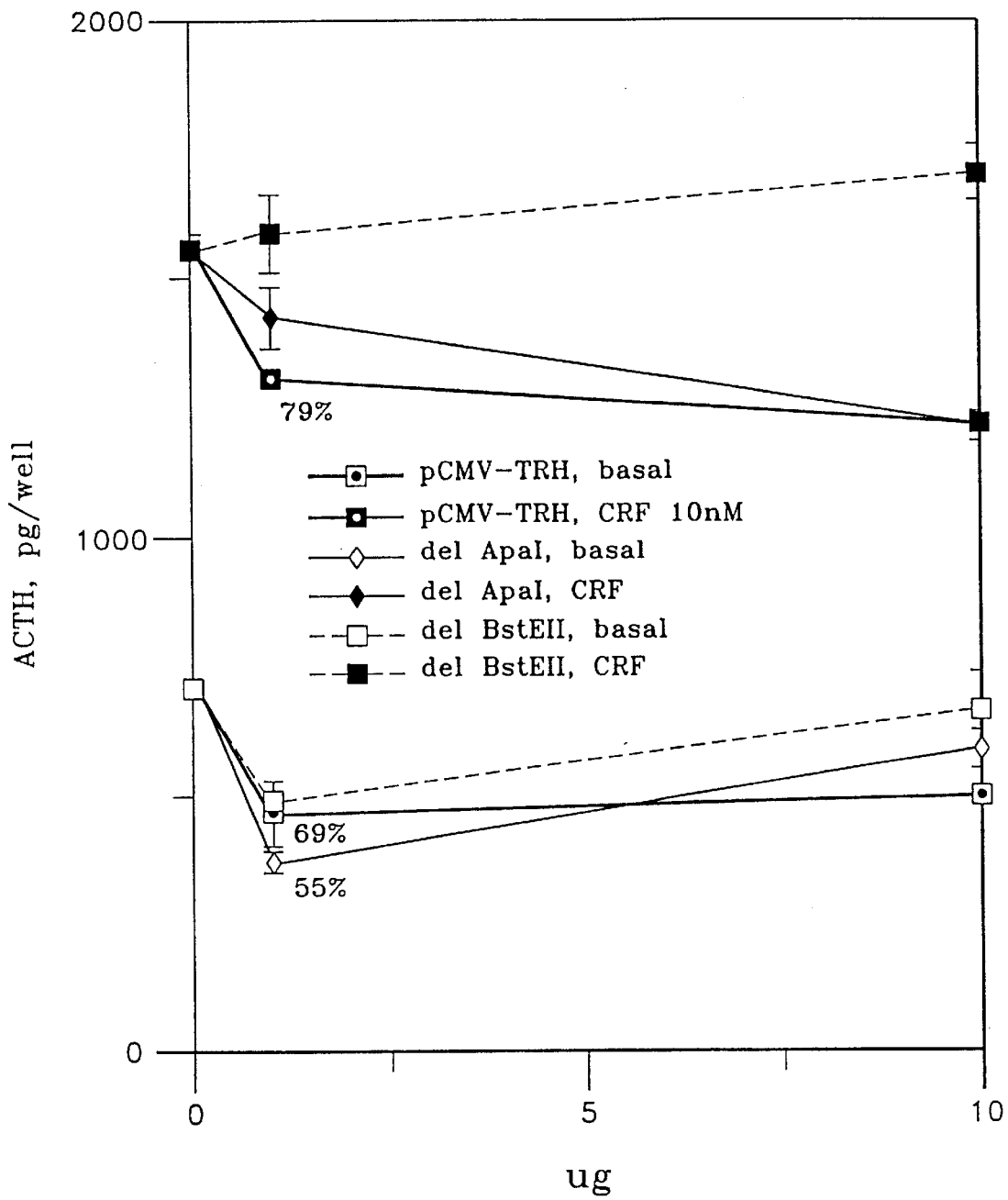
FIG. 7 is a graph depicting ACTH levels in unstimulated or CRF stimulated primary anterior pituitary cultures which are transfected with 0–10 μg of pCMV-TRH, ΔBstEII or ΔApaI, together with 0–10 gg of pcDNA3 vector, so that the total amount of plasmid DNA transfected in each lane is 10 μg.

Similar but not identical results were obtained using transiently transfected primary anterior pituitary cultures (FIG. 7). Basal ACTH secretion was reduced in primary pituitary cells which were transiently transfected with 1 μg of pCMV-TRH or with ΔApaI and to a lesser degree, these levels were also reduced in cells transfected with ΔBstEII deletions (FIG. 7). Secretion of ACTH was increased by approximately 100% following CRF stimulation (10 nM), which increase was reduced in cells transiently transfected with 1 or 10 μg of pCMV-TRH or ΔApaI, but not in cells transiently transfected with ΔBstEII (FIG. 7).

Assessment of CRIF activity in prepro-TRH intervening peptides. The intervening peptides of prepro-TRH (FIG. 1), i.e., those which do not comprise the mature TRH tripeptide, were examined for their ability to affect basal and CRF-stimulated ACTH secretion in AtT-20 cells. Peptides prepro-TRH 115–151, 160–169 and 178–199 were obtained from Penninsula Lab Inc. (Belmont, Calif.); peptides prepro-TRH 53–74, 83–106 and TRH precursor peptide (Lys-Arg-Gln-His-Pro-Gly-Lys-Arg [SEQ ID NO:11]) were obtained from American Peptide Co. Inc. (Sunnyvale, Calif.); and, peptides prepro-TRH 25–50, 208–220 and 230–255 were obtained from Quality Control QCB, Hopkington, Mass.

Figure 8:
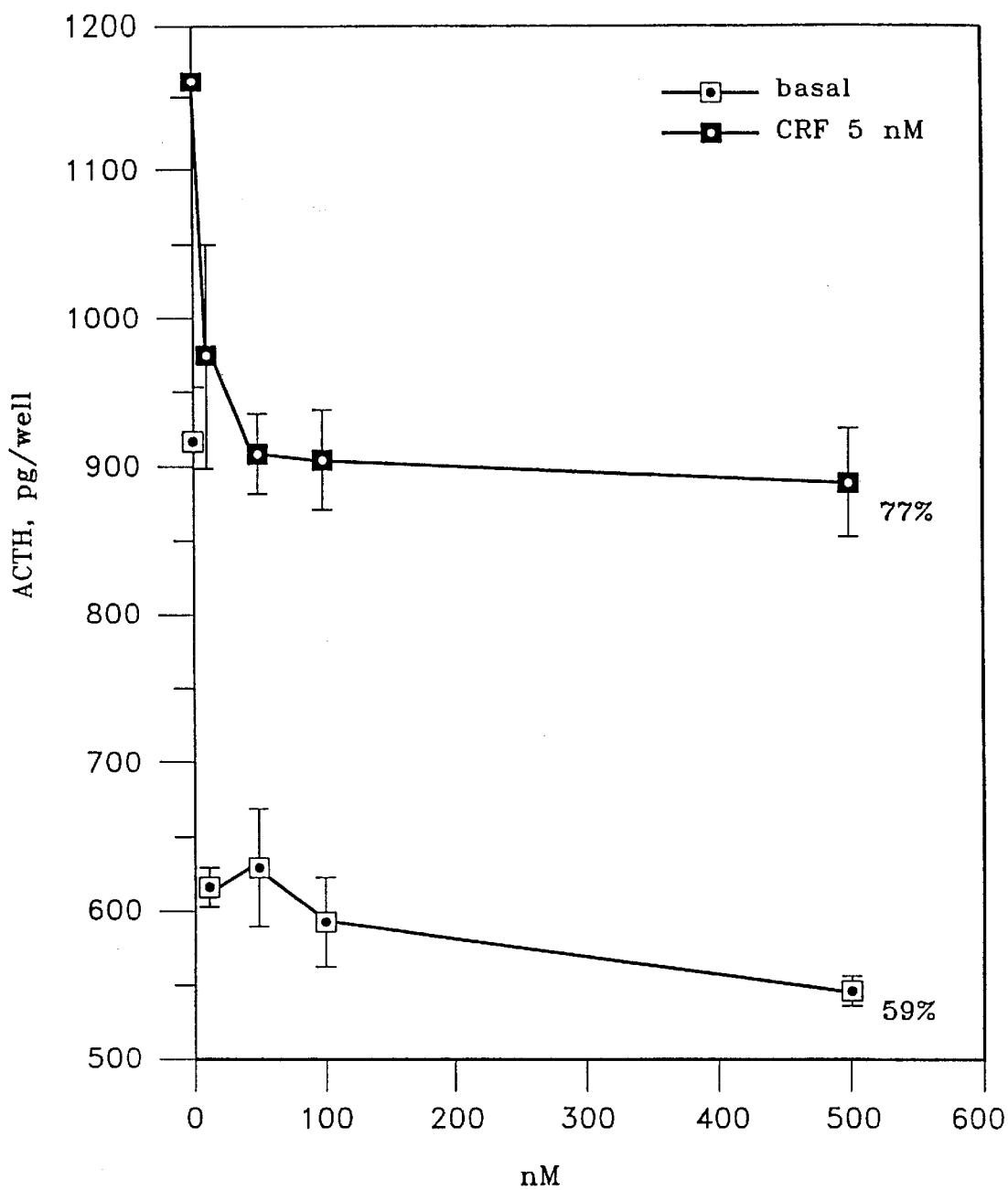
FIG. 8 is a graph depicting the effect of CRIF peptide 178–199 on the levels of ACTH in unstimulated or CRF stimulated primary anterior pituitary cells.

Peptides comprising amino acids 25–50, 53–74, 83–106, 115–151, 160–169, 178–199, 208–220 and 230–255 were individually added to AtT-20 cells and their effect on ACTH secretion was assessed. Of these peptides, only the peptide comprising amino acids 178–199 exhibited bioactivity in that both basal and CRF-stimulated ACTH secretion was reduced in their presence. Peptides comprising amino acids 178–199 and 230–250 and TRH precursor peptide were also bioassayed on primary pituitary cell cultures. In this assay, only peptide 178–199 exhibited CRIF activity in a dose response manner. The effect of peptide 178–199 on ACTH secretion in primary pituitary cultures is shown in FIG. 8.

The results of deletion studies in combination with a knowledge of the manner in which processing of prepro-TRH is known to occur, demonstrate that a peptide of amino acids 172–199, which includes the uncleaved fourth TRH portion covalently bound to the amino terminal portion of peptide 178–199, also has CRIF activity.

The results presented herein establish that a peptide residing within prepro-TRH has an inhibitory effect on both basal and CRF stimulated ACTH synthesis and secretion, which effects satisfy the requirements for CRIF activity, which peptide is therefore termed CRIF.

Figure 9:
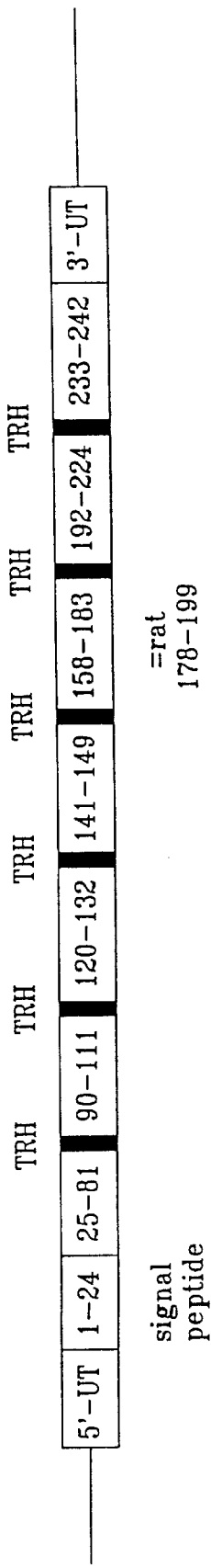
FIG. 9 is a map of the human prepro-TRH protein. Groups of amino acids are numbered beginning at the N-terminus of the molecule and the blackened areas indicate the location of each of the six mature TRH tripeptide molecules. As indicated on the figure, amino acids 158–183 in the human prepro-TRH protein correspond to amino acids 178–199 in the rat prepro-TRH protein.

A map of the human prepro-TRH protein is shown in FIG. 9, which protein shares significant similarities with the rat prepro-TRH protein (FIG. 10). In fact, rat, human and mouse prepro-TRH and in particular, that portion of prepro-TRH which constitutes CRIF, share significant homology with each other. Thus, the invention specifically includes human and mouse CRIF, in addition to rat CRIF. Given the similarities observed between rat, human and mouse CRIF sequences, and the data provided herein establishing that the activities of CRIF from these species is virtually identical, the invention must also be construed to include all mammalian CRIFs.

The fact that a corticotropin release inhibiting peptide shares a precursor with TRH suggest a new model for hypothalamic control of ACTH and TSH secretion. According to this model, the secretion of these pituitary hormones is coupled through the influence of the two hypothalamic peptides, TRH and CRIF, produced from a single precursor molecule expressed from a gene in a discreet population of hypothalamic neurons. Because of the opposite regulatory actions of these two peptides on their respective pituitary target cells, namely that TRH stimulates pituitary thyrotrophs to secrete thyroid-stimulating hormone (TSH), while CRIF inhibits ACTH, the model predicts that TSH and ACTH levels are inversely related. Therefore, when prepro-TRH containing neurons secrete higher levels of TRH and CRIF, plasma TSH levels will be elevated and ACTH levels will be reduced. Conversely, low output of TRH and CRIF will lead to reduced plasma levels of TSH and elevated levels of ACTH. Indeed, the former situation occurs in hypothyroid states when hypothalamic prepro-TRH mRNA levels are increased (Segerson et al., 1987, Science 238:78), and the latter situation is observed when hypothalamic prepro-TRH mRNA levels are decreased in animals in a hyperthyroid state (Kakucbka et al., 1992, Endocrinology 130:2845).

Production of CRIF. To produce CRIF in large amounts, a eukaryotic cell line is transfected with a plasmid encoding CRIF wherein transcription of CRIF is placed under the control of a promoter capable of constitutively or inducibly driving expression of CRIF in the cell. The procedures for transfection are described herein and other procedures which may be used are known and are described, for example, in Sambrook et al. (1989, Molecular Cloning: A Laboratory Manual, Cold Spring Harbor, N.Y.). Constitutive promoters which may be used include the human cytomegalovirus immediate early promoter, the Rous sarcoma virus long terminal repeat promoter sequences and the like; inducible promoters include those which are induced in the presence of metal, tetracycline, or other inducers known to those skilled in the art and also described in Sambrook et al. (1989, Molecular Cloning: A Laboratory Manual, Cold Spring Harbor, N.Y.).

Preparation of a transfection vector containing the human prepro-TRH gene. The gene encoding human prepro-TRH (hTRH) cloned into pGEM-4Z was used as the starting vector (Yamada et al., 1990, Molec. Endrocrinol. 4,4, 551–557). This plasmid contains the complete prepro-TRH transcription unit, i.e., the full length gene including the promoter sequence. To prepare a vector for transfection of hTRH into AtT-20 cells, the plasmid pcDNA3 (5.4 kb) was modified as follows. The CMV promoter sequences were deleted by digestion with BglII and BamHI. The plasmid was recircularized by ligation of the resulting cohesive termini. The hTRH gene was excised from the hTRH-containing pGEM-4Z plasmid by digestion with EcoRI and was inserted into the EcoRI site of the modified pcDNA3 vector giving rise to the plasmid, pcDNA3(4.5 kb)-hTRH. This plasmid was propagated in *E. coli* MC1061 (Invitrogen).

Construction of a CRIF-minigene. A minigene having rat CRIF sequences expressing CRIF activity, which does not comprise TRH sequences was constructed as follows. A total of 227 base pairs having an 18 base pair multiple cloning restriction enzyme site positioned 5' to a 50 base pair 5' region of a preproTRH gene (wherein the first base pair is at position +1 of the preproTRH sequence), which is positioned 5' to 24 base pairs of preproTRH signal sequence, which is positioned 5' to 66 base pairs of CRIF coding sequence, which is positioned 5' to 9 base pairs of a translational stop codon, which is positioned 5' to an 18 base pair multiple cloning restriction enzyme sequence were ligated together using standard recombinant DNA technology. This minigene was positioned downstream from the human cytomegalovirus promoter/regulatory region within the vector pcDNA 3.

Human prepro-TRH encodes CRIF activity. To establish that the human prepro-TRH also encodes CRIF activity, a series of transfection experiments were conducted. Mouse cortitroph AtT-20 cells were either transiently or stably transfected with the human prepro-TRH gene using the transfection procedures described herein. Cells which were transiently transfected with the gene exhibited significant inhibition of both ACTH secretion and POMC expression when compared with cells which were transfected with vector alone. Furthermore, an inverse correlation between TRH gene expression and ACTH secretion was observed in cells stably transfected with human prepro-TRH.

The rat lactotroph cell line, GH3, was also stably transfected with human preproTRH to provide yet another cellular model for investigation of human CRIF activity within the human prepro-TRH gene. Given the fact that CRIF lies within prepro-TRH and must be cleaved therefrom, this cell line was chosen in order to determine the effect of the cellular processing machinery on CRIF activity. CRIF activity in GH3 cells was assessed in a bioassay designed to measure ACTH secretion using AtT-20 cells as a target. The results of these experiments are described below.

Conditioned medium obtained from GH3 cells stably transfected with human prepro-TRH suppressed ACTH secretion in AtT-20 cells. In contrast, conditioned medium obtained from mock-transfected cells (i.e., cells transfected with vector alone) had no effect on ACTH secretion in AtT-20 cells. In addition, GH3 cells which were transfected with human prepro-TRH responded to $T_3$ treatment at a concentration of 1–100 nM by suppressing expression of TRH mRNA. These data therefore establish that expression of preproTRH and subsequently secretion of ACTH, may be regulated in cells having thyroid hormone receptors.

Figure 11B:
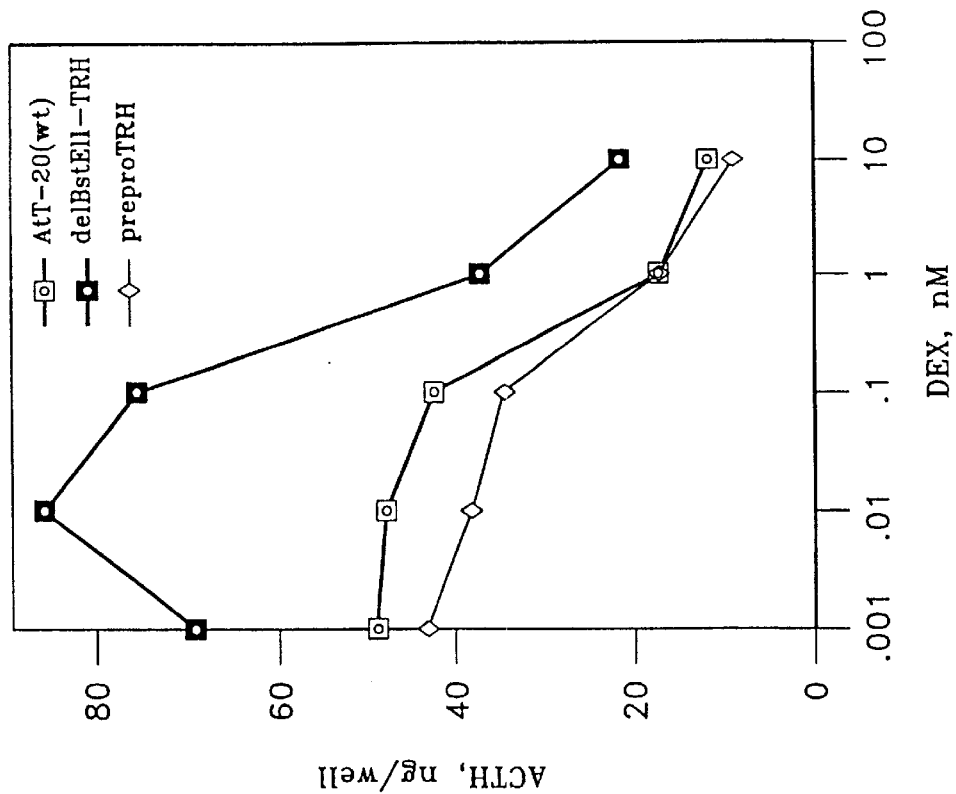
FIG. 11, comprising parts A and B, is a series of graphs depicting secretion of ACTH in untransfected AtT-20 cells or in cells transfected with prepro-TRH (A) or ΔBstEII (B), to which cells was added dexamethasone.

The effect of dexamethasone on ACTH secretion in AtT-20 cells stably transfected with rat prepro-TRH or with ΔBstEII. Cells which are stably transfected with prepro-TRH cDNA and are therefore continuously producing prepro-TRH 178–199 should exhibit an increased inhibition of ACTH secretion following dexamethasone treatment. To confirm that this is the case, untransfected AtT-20 cells and a clone of rat prepro-TRH stably transfected AtT-20 cells, which clone exhibited high levels of expression of prepro-TRH, were seeded into wells at a concentration of $5 \times 10^5$ cells/ml of DMEM and 10% fetal calf serum. Cells were washed and treated with dexamethasone (DEX) at concentrations of 1, 10, 100 or 1000 nM for 24 hours in medium supplemented with 10% steroid-free fetal calf serum. The supernatant was harvested and the amount of ACTH contained therein was measured and the results are presented in FIG. 11.

Figure 11A:
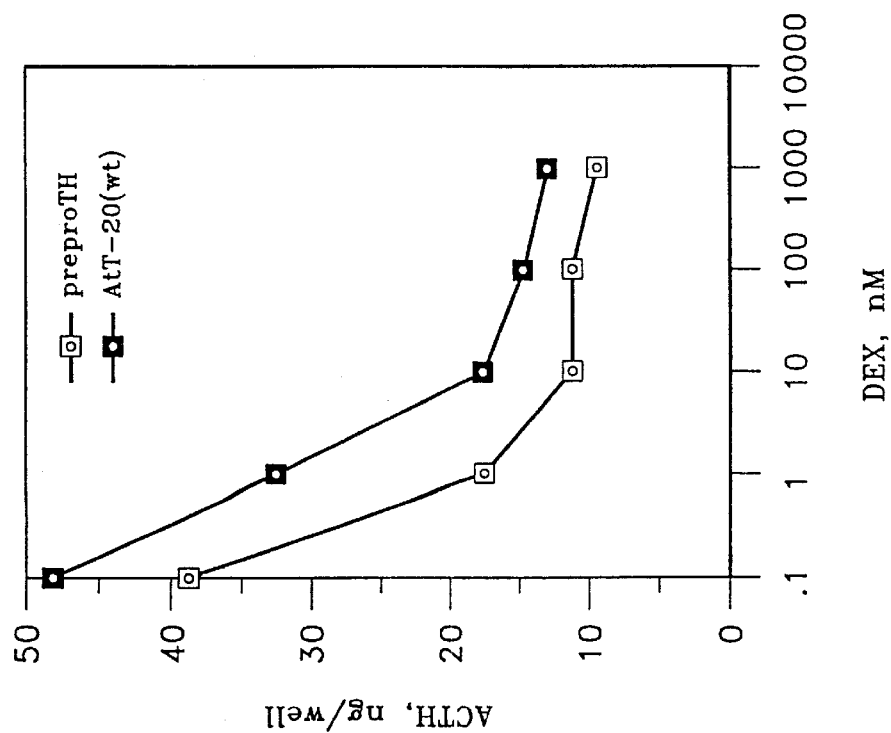

Although the basal levels of ACTH secretion were lower in prepro-TRH transfected cells than in untransfected cells, treatment with DEX suppressed ACTH secretion in both untransfected and in transfected cells in a dose response manner. However, DEX treated transfected cells exhibited a higher level of inhibition of ACTH secretion than did untransfected cells and this inhibition was most marked at lower concentrations of DEX (FIG. 11A). This experiment was repeated using less cells per well ($5 \times 10^4$ cells/well) with essentially the same results. In contrast to the above, cells which were transfected with ΔBstEII exhibited no inhibition of ACTH secretion following treatment with low concentrations of DEX. Thus, DEX-induced inhibition of ACTH secretion of prepro-TRH transfected cells reflects the additional inhibitory effects of constitutively secreted prepro-TRH 178–199 on ACTH secretion.

The effect or CRIF on the development of rheumatoid arthritis. The data presented below establish that CRIF contributes to the development of rheumatoid arthritis (RA) by diminishing the activity of the HPA axis.

RA is an autoimmune disease characterized by chronic degradation of the joints resulting from inflammation of synovial membranes. SCW-induced inflammation in the autoimmune prone female Lewis rat is an accepted animal model for the study of RA. In this animal, susceptibility to the inflammatory response is greatly enhanced by the fact that it has a defective HPA axis and low glucocorticoid levels. It is likely that increased thyroid activity decreases the susceptibility to inflammatory immune disease by increasing glucocorticoid levels. The discovery of CRIF encoded within the same precursor as TRH establishes a direct link between the HPA and thyroid axes. Thyroid hormones may play a fundamental role in regulating the HPA axis by modulation of levels of prepro-TRH mRNA. In fact, thyroxin ($T_4$) treatment decreases the adverse inflammatory effects of SCW-induced autoimmune responses (Rittenhouse et al., $77^{th}$ Endocrine Society Meeting, 1995).

To determine the role played by thyroid hormones and concomitant changes in the HPA axis in the development of SCW-induced inflammatory response, expression of genes which reflect the status of thyroid function (TRH), pituitary-adrenal activity (POMC) and inflammation (IL-1β and MIP-1α, a macrophage specific inflammatory protein) was measured. Adult female rats were fed a regular diet (control), or a regular diet plus 0.012% $T_4$ (hyperthyroid) or 0.05% 6-propyl-thiouracil (PTU) supplied in the in drinking water (hypothyroid), for seven weeks. A preparation of SCW (20 μg/g of body weight) was administered intraperitoneally to the rats three days before decapitation. Anterior pituitary POMC, hypothalamic TRH and peritoneal macrophage IL-1β and MIP-1α mRNA levels were assessed by Northern blot hybridization analysis using specific cDNA probes. The levels of mRNA were normalized to the housekeeping gene, GAPD, and were quantified by image analysis densitometry. Plasma levels of TSH and CORT were determined by RIA. The results are presented in FIG. 12.

The levels of TRH mRNA were decreased by 20% in the hyperthyroid group of animals and were increased by 52% ($p<0.01$) in the hypothyroid group (FIG. 12A). Injection of SCW resulted in an increase in TRH mRNA levels in control and hyperthyroid rats and in a decrease in TRH mRNA levels in hypothyroid rats. In contrast, each of the groups of rats exhibited the opposite pattern with regard to levels of POMC mRNA in response to altered thyroid status (FIG. 12B). This is indicative of increased pituitary adrenal activity in hyperthyroid and decreased pituitary adrenal activity in hypothyroid rats and suggests a direct connection between the HPA and thyroid axes.

Figure 12D:
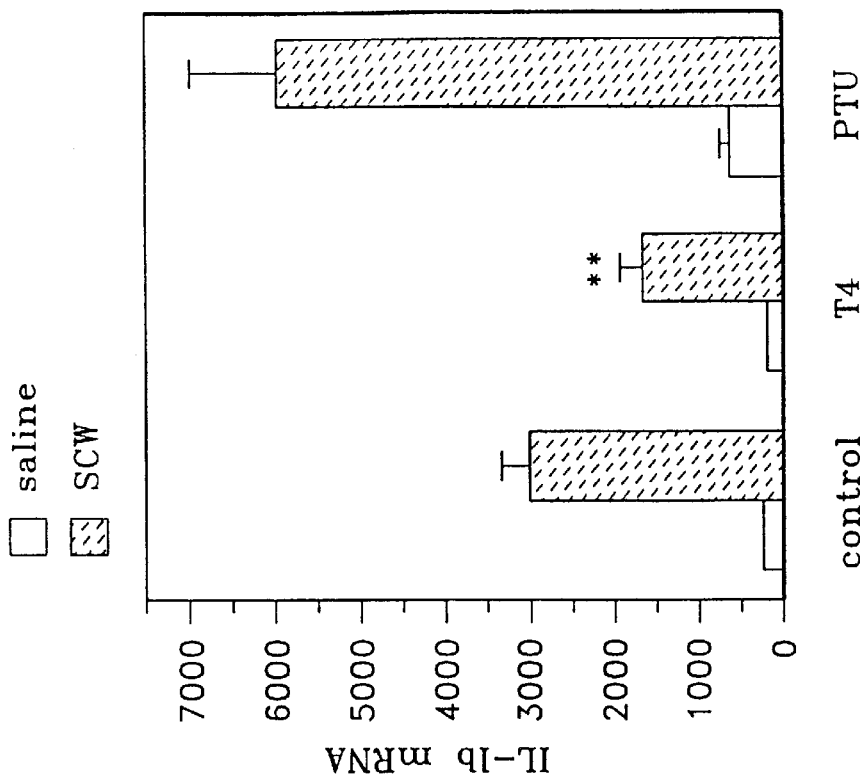
FIG. 12, comprising parts A, B, C, D and E, is a series of graphs depicting expression of TRH/GAPD mRNA (A), POMC/GAPD mRNA (B), MIP1α mRNA (C) and IL-1β mRNA (D) and, production of plasma corticosterone steroid hormone (E) in control rats or in hypo- or hyperthyroid rats, following administration of streptococcal cell wall (SCW) preparation.
Figure 12C:
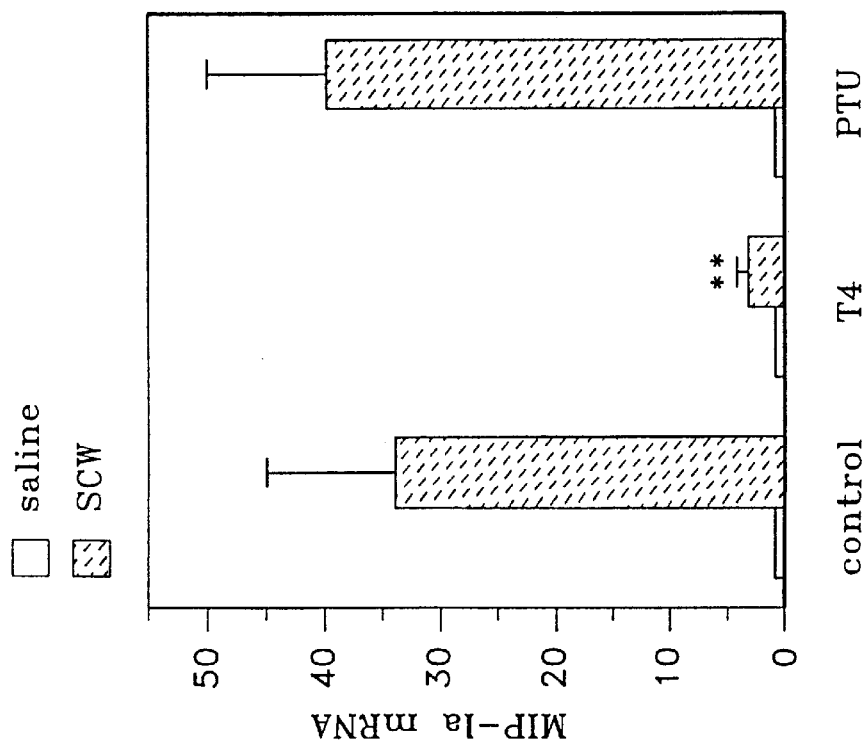
Figure 12E:
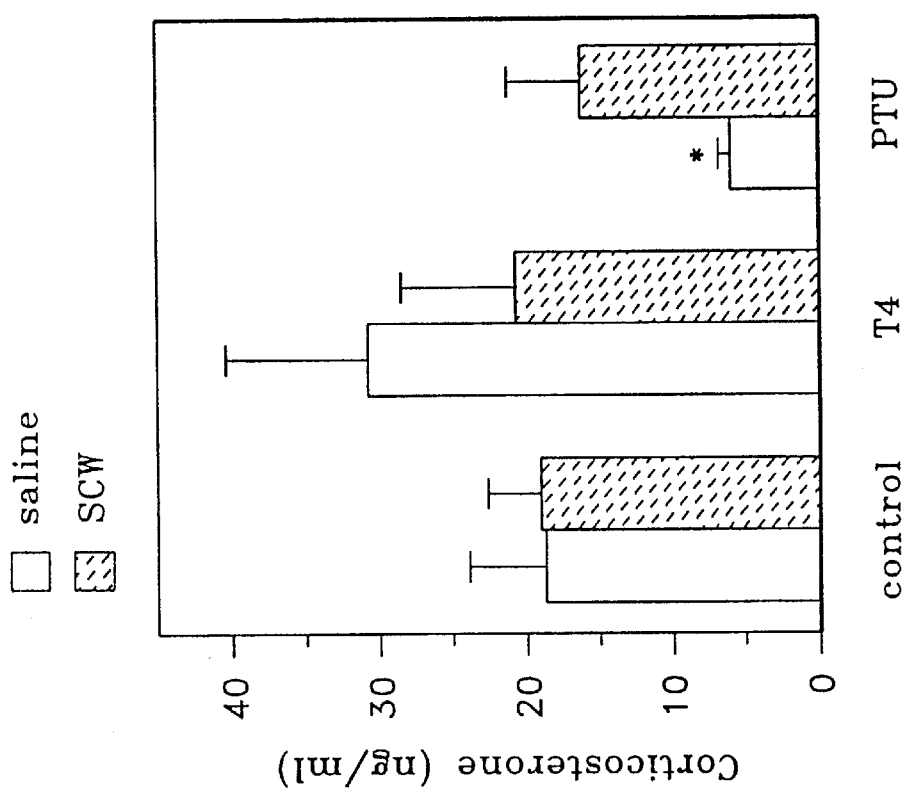
Figure 13B:
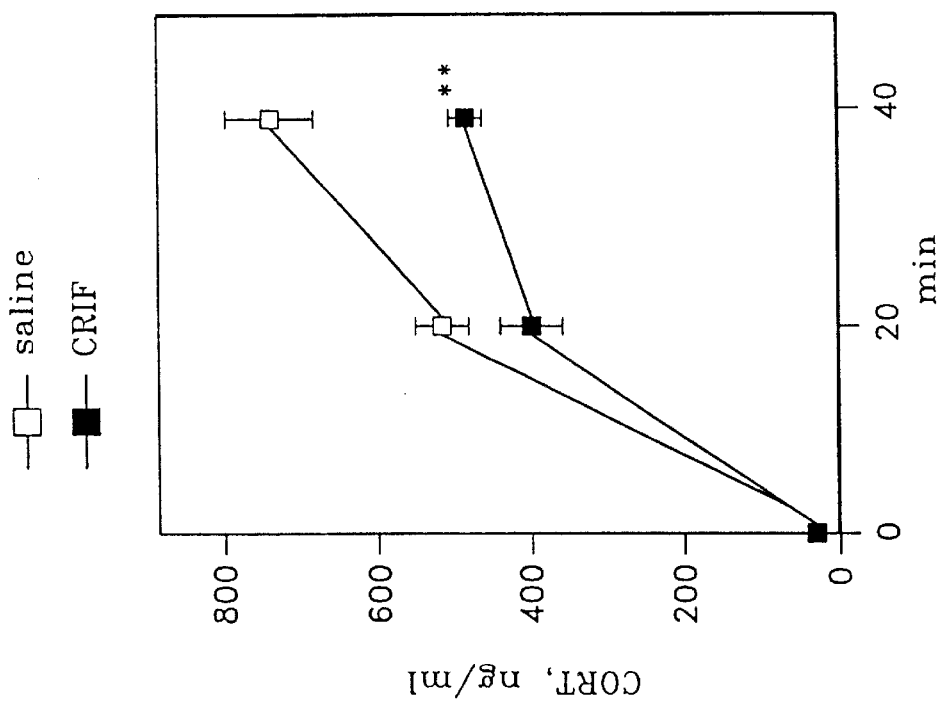
FIG. 13, comprising parts A, B, C and D, is a series of graphs depicting the in vivo corticosterone response and anti-depressant effects of CRIF in rats undergoing the Porsolt swim test and which have been administered CRIF. (A) resting rats; (B) swim-stressed rats; (C) floating time in swim-stressed rats; and, (D) struggling time in swim-stressed rats.
Figure 13A:
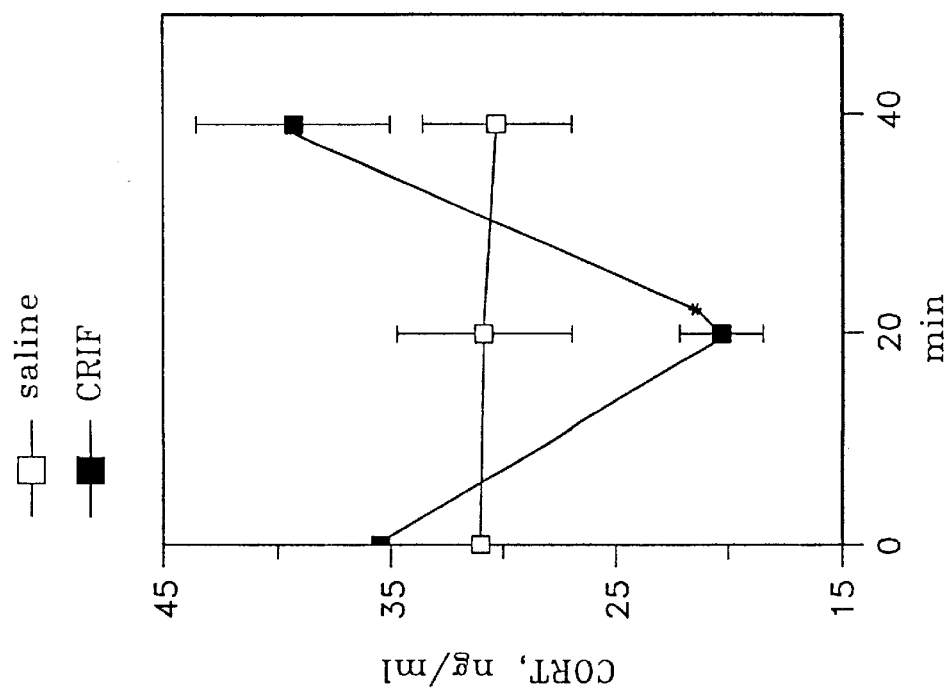
Figure 13D:
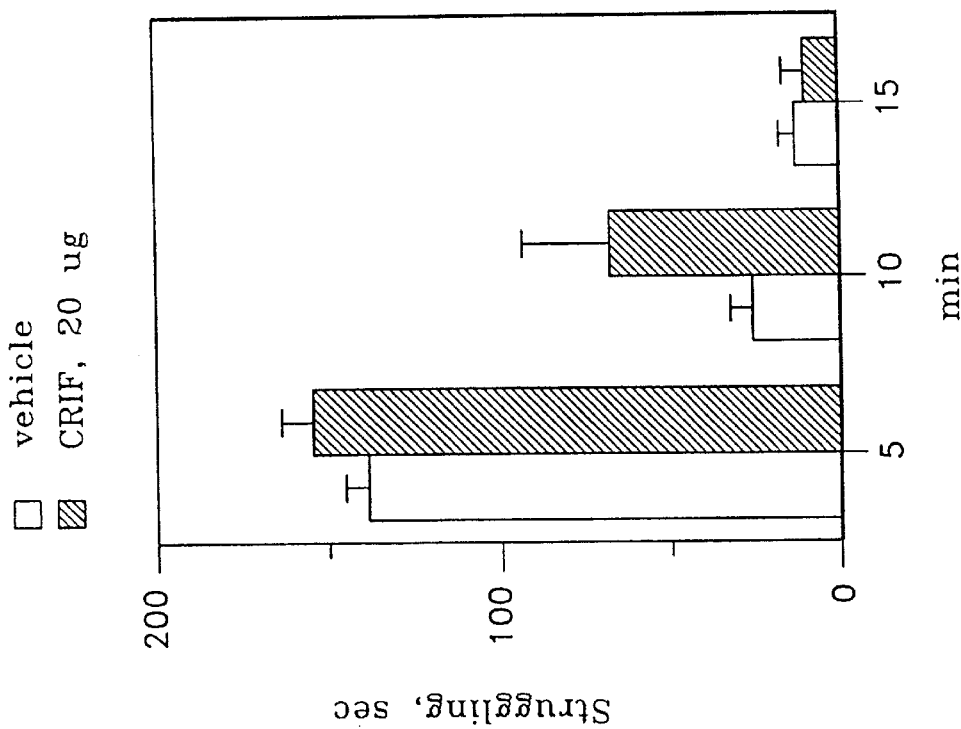
Figure 13C:
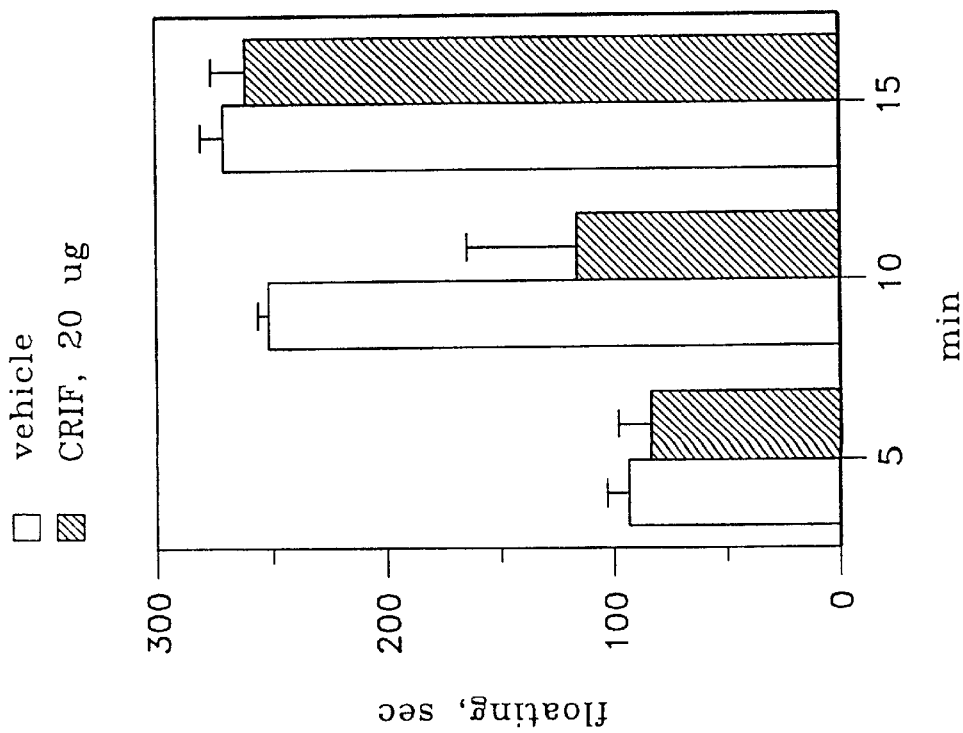

When presented with an inflammatory insult (i.e., SCW), macrophages become activated and secrete an array of cytokines such as MIP-1α and IL-1β. In control non-SCW-administered rats, MIP-1α a was not detected in macrophages whereas in SCW-administered control rats, a dramatic (17-fold) induction of MIP-1β mRNA was observed (FIG. 12C). When hypothyroid rats were administered SCW, an even greater (22-fold) increase in MIP-1α mRNA levels was observed, whereas hyperthyroid rats exhibited only a 1.7-fold increase in MIP-1α levels when administered SCW. A similar pattern of expression of IL-1β was observed in untreated and SCW-treated rats (FIG. 12D). These data establish that the hypothyroid state exacerbates while the hyperthyroid state diminishes the inflammatory effects of SCW. Hypothyroid rats exhibited a significant decrease in plasma CORT levels and hyperthyroid rats exhibited a significant increase in plasma CORT levels (FIG. 12E). These latter results reflect the endogenous glucocorticoid milieu. To confirm the thyroid status of the rats, plasma levels of TSH were measured and were correlative of the expected thyroid status of each of the different groups of rats.

The data just provided establish that a CRIF antagonist may be used to treat an animal having an inflammatory disease to alleviate or ablate that disease. These data further establish that either of $T_3$ or $T_4$ may be administered in the absence of a CRIF antagonist and have the same effect, i.e., administration of $T_3$ or $T_4$ in the absence of a CRIF antagonist may also reduce the severity of or even ablate inflammatory disease in an animal.

Inhibition of basal and swim-stress induced CORT in rats treated with CRIF in vivo. To assess the ACTH release inhibitory activity of prepro-TRH 178–199 in vivo, 20 μg of prepro-TRH 178–199 was administered intravenously into freely moving Wistar rats under resting conditions and immediately prior to forced swim stress. Prior to administration, a vascular access port was implanted in the rats, which port was connected to a catheter inserted into the right jugular vein (Redei et al., 1994, Neuroendocrinology 60:113–123). Two days following implantation, the rats were provided with a 2 hour acclimatization period and a basal blood sample of 0.5 ml was obtained through an extender connected to the port. The rats were then administered 20 μg of CRIF in a 100 μg/ml solution of saline. The rats were divided into groups. Additional blood samples were obtained at 20 and 40 minutes following administration of CRIF or vehicle from one group of rats which were undisturbed. A second group of animals were forced to swim for 15 minutes in 25° C. water, they were dried and were returned to their cages. Blood samples were also obtained from these rats at 20 and 40 minutes from the time at which the swim stress was initiated. Plasma ACTH and CORT levels were determined in each of the samples by RIA.

The CORT response to CRIF administration in resting (A) and stressed (B) rats is shown in FIG. 13, parts A and B. Administration of CRIF inhibited, to a significant degree ($p<0.01$), both resting and stress-induced CORT levels in the rats. Further, CRIF administration effected a decrease in the time the rats spent floating (FIG. 13C) and increase in the time the rats spent struggling (FIG. 13D) in the second 5 minutes of the 15 minute Porsolt swim test, suggesting that CRIF effects a decrease in depressive behavior.

Inhibition of ACTH and CORT response to footshock stress in rats treated with CRIF in vivo. Increasing amounts of prepro-TRH 178–199 were administered to freely moving adult male Wistar rats (300–350 g) prior to exposure to intermittent footshock stress using the experimental protocol similar to that described above. The animals were cannulated as described and two days later they were subjected to intermittent footshock stress (0.2 mA, 15 seconds, 0.5 seconds on and 0.5 seconds off) immediately following intravenous administration of saline or of increasing amounts of prepro-TRH 178–199. Resting (non-shocked) animals also served as controls. Blood samples were obtained as described and plasma levels of ACTH and CORT were assessed in the same. The results are presented in FIG. 14. Plasma levels of ACTH were significantly reduced in stressed animals which had been administered CRIF (FIG. 14A). Inhibition of plasma CORT levels by prepro-TRH 178–199 was even more marked than inhibition of ACTH and was evident even at lower doses of prepro-TRH 178–199 (FIG. 14B).

Restraint Stress produces region specific changes in rat brain CRIF. The data now presented establish that the concentration of CRIF in rat brain is altered in specific regions of the brain in response to stress.

A specific radioimmunoassay was developed having a sensitivity of 19 pg/tube using a polyclonal antibody and $^{125}$I-Tyrosine$^{178}$-CRIF as a tracer. The polyclonal antibody was generated following immunization of rabbits with CRIF conjugated to bovine serum albumin. $^{125}$I-Tyrosine-CRIF was obtained using the chloramine-T method. Since Tyrosine-CRIF is bioactive in AtT20 cells (i.e. exhibited CRIF activity in these cells), $^{125}$I-Tyrosine-CRIF is predicted to be biologically active in AtT20 cells. Thus, $^{125}$I-Tyrosine-CRIF is also useful for isolation of a CRIF receptor using standard receptor binding assays.

Particular regions of the rat brain were dissected from adult male rats (n=6 per group) at either 9:00 am or 9:00 pm at 30, 90 and 180 minutes following thirty minutes of restraint stress. The amount of CRIF in each region of the brain was measured using the above described radioimmunoassay.

CRIF (ng/mg of total protein) was found in different regions of the brain in the following concentrations: Hypothalamus 9.2; septum 6.3; caudate 2.9; amygdala 0.82; prefrontal cortex 0.75; and periaquaductal grey (PAG) 0.6. The highest amount of CRIF was found in the median eminence (ME) being present at a concentration about five-fold greater than that found in the hypothalamus. A negligible amount of CRIF was found in several other brain tissues tested. A diurnal morning decrease of CRIF was observed in the ME, pituitary and septum; however, CRIF was increased in PAG in the morning.

Following stress, change in CRIF content in specific regions of the brain was observed ($F_{[5,16]}=1.98$, $p<0.05$). At 30 minutes, a small increase in CRIF concentration was observed in the hypothalamus, septum, caudate and amygdala followed by a decrease in the hypothalamus, caudate and amygdala at 90 and 180 minutes post-stress. In the prefrontal cortex and PAG, CRIF concentrations were decreased in response to stress in the absence of any initial increase. In contrast, CRIF concentrations were increased in the ME and pituitary at all times examined post-stress.

These data establish that the radioimmunoassay described herein provides an efficient test for measurement of CRIF in brain. The data also establish that CRIF concentrations in brain vary in different regions of the brain following the application of stress.

Figure 15A:
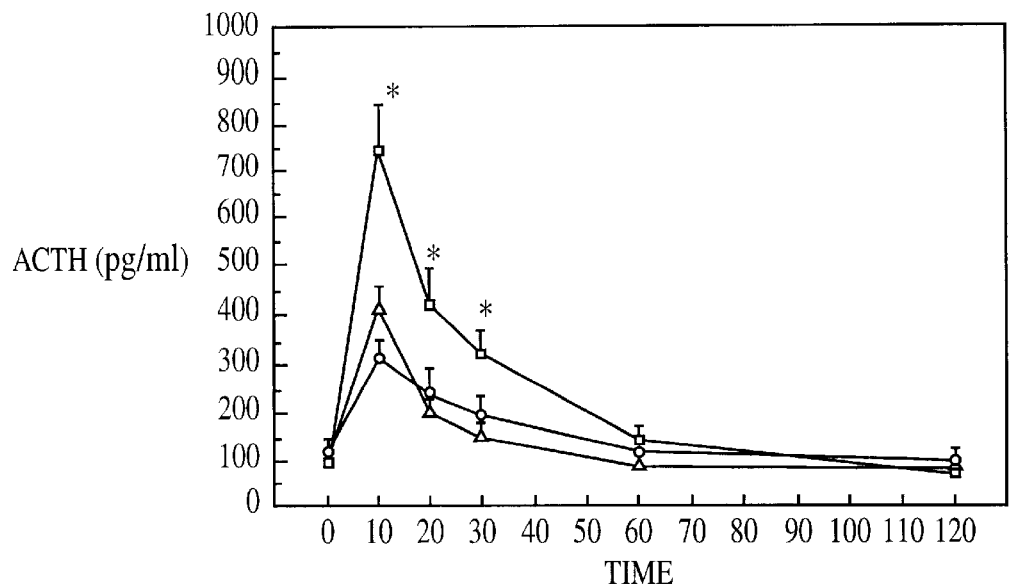
FIGS. 15A, 15B, and 15C, is a trio of graphs depicting the in vivo effects of CRIF on ACTH, corticosterone and prolactin levels in rats which were subjected to restraint stress. Animals were injected intravenously (iv) with CRIF or the vehicle 5 minutes prior to the restraint period. Serial blood samples were obtained at 10, 20, 30, 60 and 120 minutes following stress onset. (A) ACTH, (B) corticosterone (CORT) and (C) prolactin (PRL) levels were measured by radioimmunoassay.
Figure 15B:
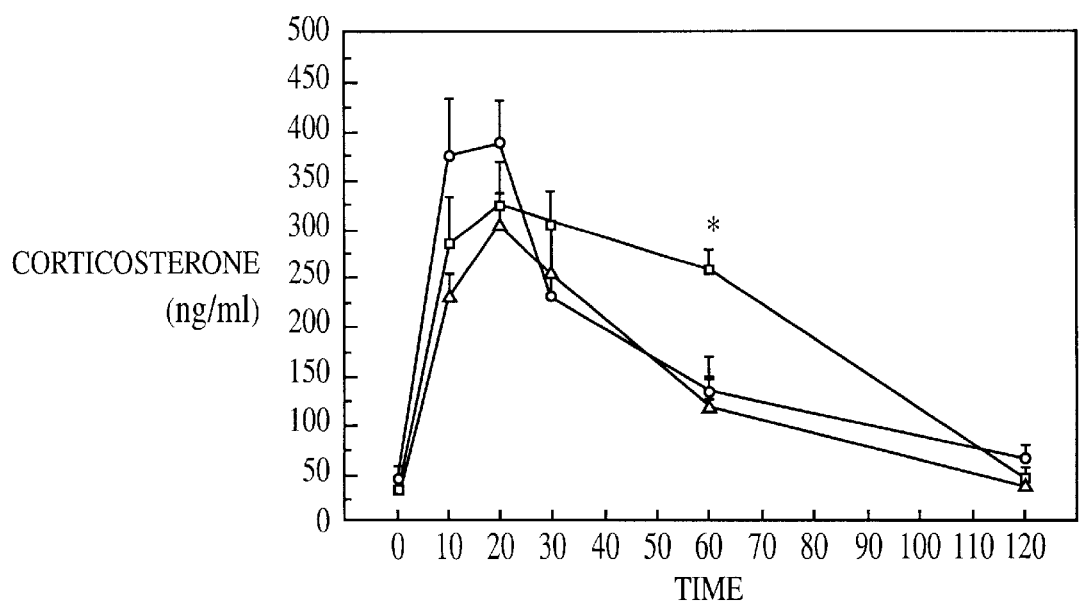
Figure 15C:
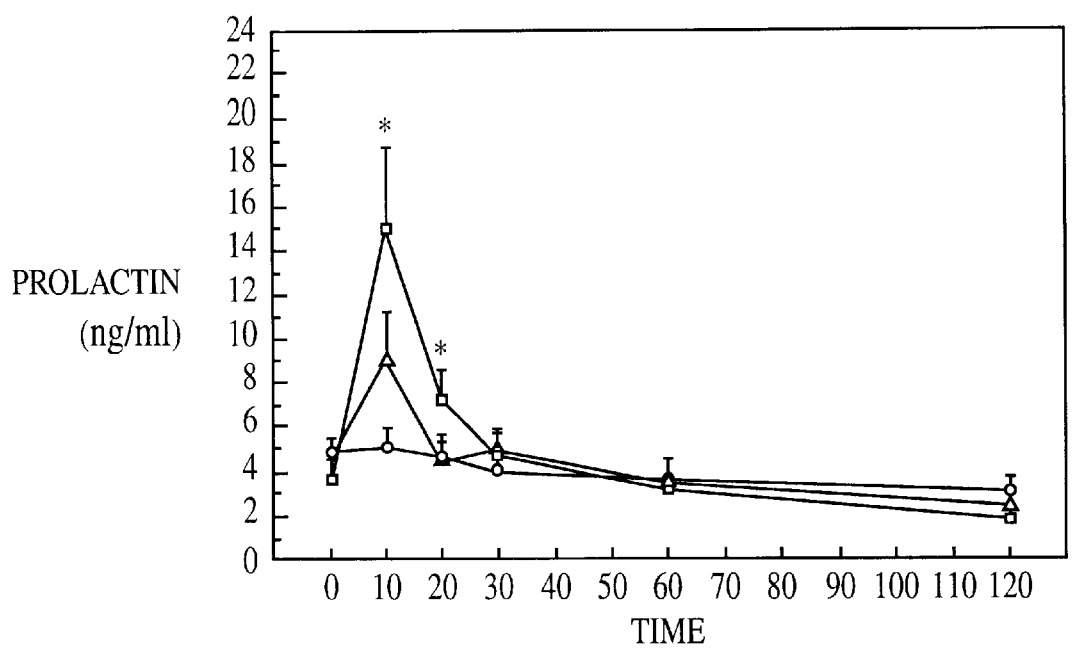

The effect of CRIF on prolactin secretion. The ability of CRIF to inhibit stress-induced hormone secretion was examined in rats exposed to restraint stress for 5 minutes. Animals were injected intravenously (iv) with CRIF or the vehicle in the absence of CRIF 5 minutes prior to the restraint period. Serial blood samples were obtained at 10, 20, 30, 60 and 120 minutes following the onset of stress. ACTH, corticosterone (CORT) and prolactin (PRL) levels were measured by radioimmunoassay (Van de Kaar et al., 1982, Neuroendocrinology 35:225–230). Following iv administration, CRIF significantly inhibited the stress-induced rise in ACTH, CORT and PRL (FIG. 15 A, B and C). CRIF administration did not influence basal prolactin secretion, indicating that its effects are not due to an increase in dopaminergic tone. Thus, CRIF has a marked affect on secretion of prolactin and therefore may be used to treat diseases associated with increased secretion of prolactin.

Figure 16A:
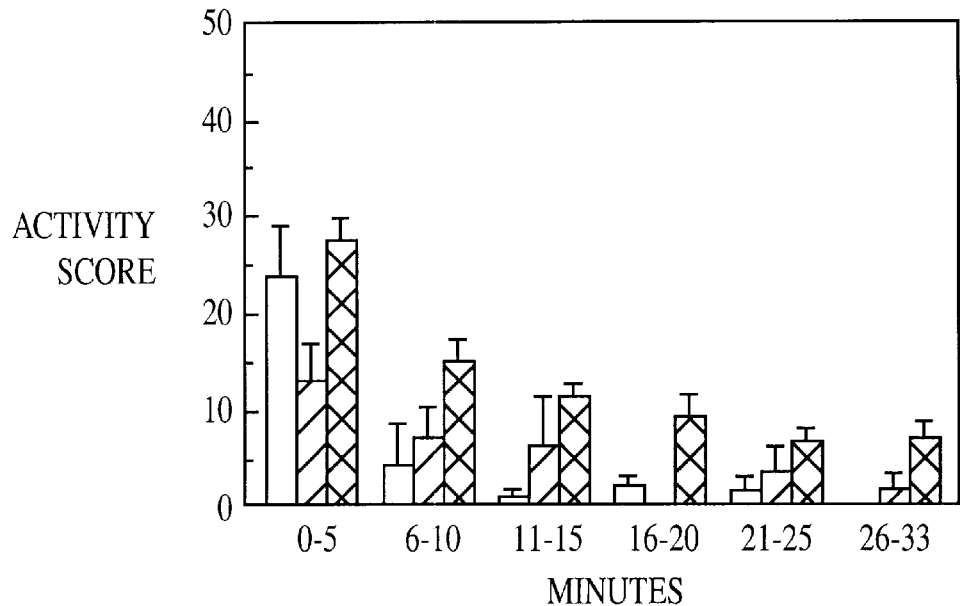
FIGS. 16A, 16B, 16C, and 16D, is a series of graphs depicting the effects of CRIF on the behavior of rats in vivo in an open field test. The animals were placed in the center of a 15 inch diameter open-field 5 minutes following intracerebroventricular (icv) administration of CRIF. The subsequent behavior of the animals was videotaped for a 30 minute period.
Figure 16B:
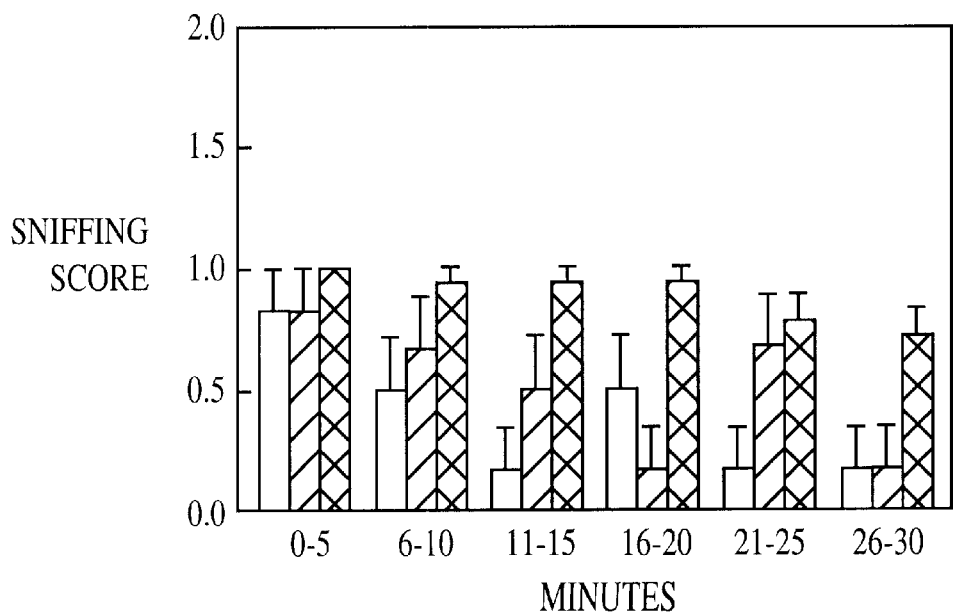
Figure 16C:
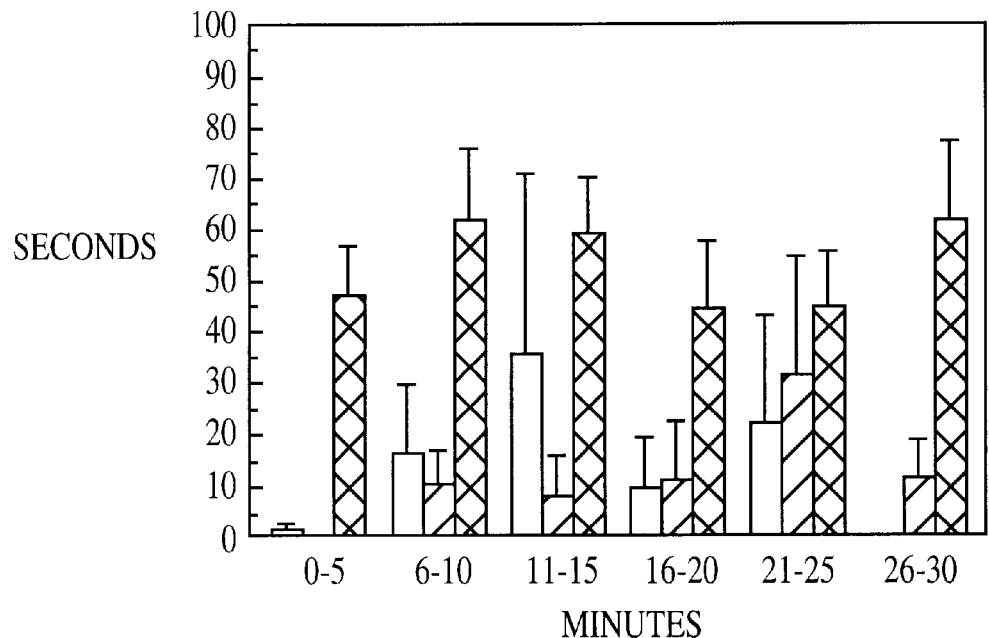
Figure 16D:
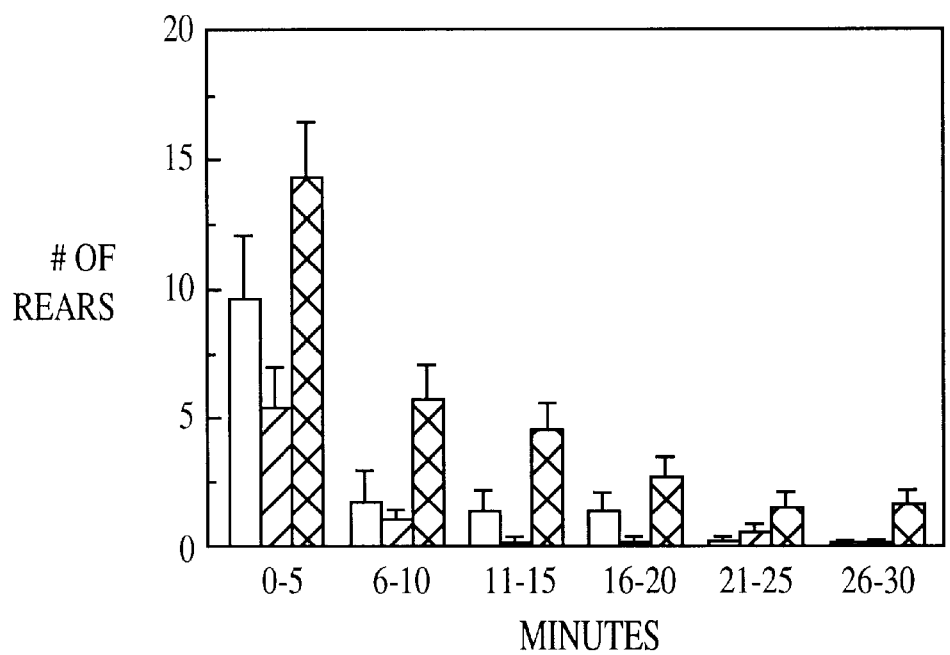

Behavioral effects of in vivo administered CRIF. An open field test was conducted to examine the effects of CRIF on the behavior of test animals placed in a novel environment. Rats were placed in the center of a 15 inch diameter open-field 5 minutes after intracerebroventricular (icv) administration of CRIF, and their behavior was videotaped for 30 minutes. Analyses revealed a rapid habituation of behaviors over the 30 minute period in vehicle treated animals. In contrast, animals administered CRIF at a dose of 6 µg/kg exhibited significant increases in activity, sniffing, grooming behavior and rearing during this period compared with the vehicle treatment (FIG. 16A, B, C and D). Little or no behavioral effect was observed in response to a lower dose of CRIF (0.6 µg/kg).

Figure 17B:
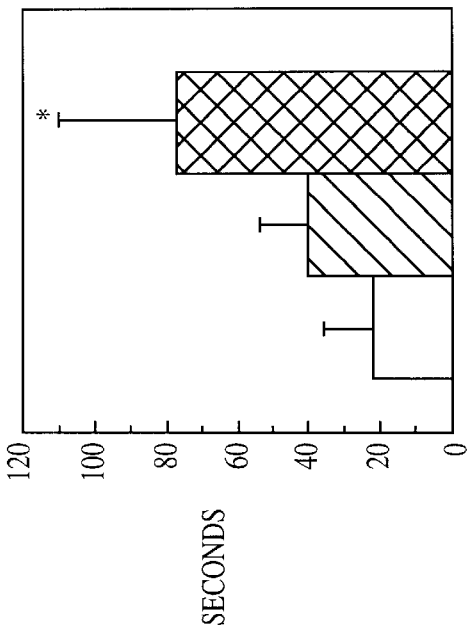
FIGS. 17A, 17B, and 17C, is a series of graphs depicting the anxiolytic properties of CRIF when administered to a rat in vivo. Rats were tested using a light/dark box. Five minutes prior to testing, the animals were injected icv with CRIF or the vehicle. At the beginning of testing, each animal was placed in the center of the light compartment. Behavior was subsequently videotaped for 15 minutes. The behaviors exhibited by the rats were scored by a trained observer who was unaware of the treatment status of each rat. The measures scored were (in FIG. 17A) initial latency to enter the dark compartment.
Figure 17C:
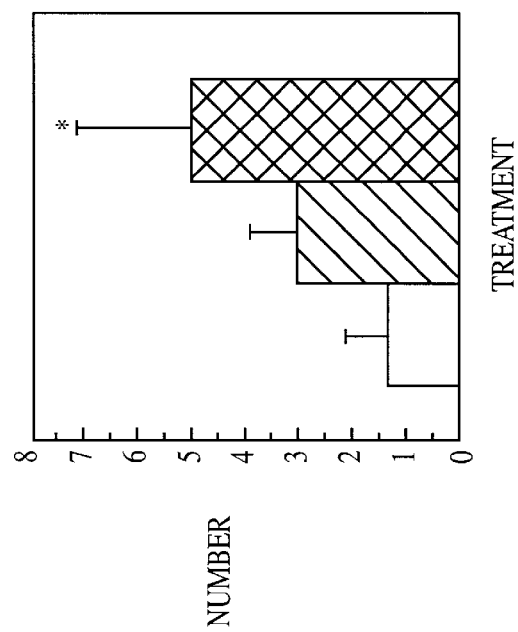
Figure 17A:
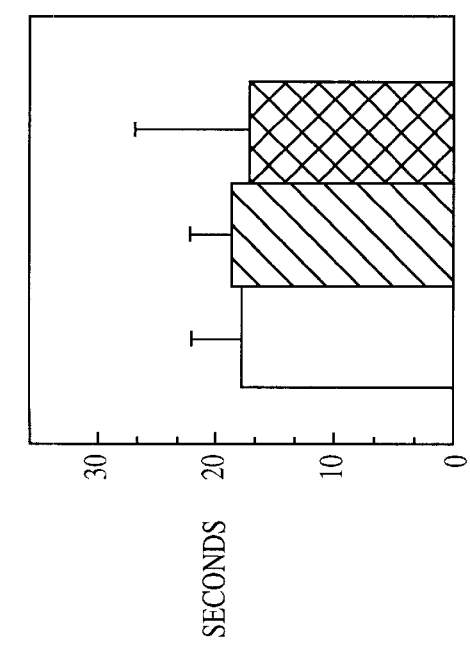

The anxiolytic properties of CRIF were tested using a light/dark box. The box is a plexiglass chamber divided into a lighted compartment connecting to an adjoining dark compartment. The test exploits the rodent's natural conflict between avoidance and exploration of lighted, open areas. Five minutes prior to testing, the animals were injected icv with CRIF or the vehicle alone. At the beginning of testing, each animal was placed in the center of the light compartment. Behavior was subsequently videotaped for 15 minutes. The behavior of the animals was scored by a trained observer who was unaware of the treatment status of each animal. The behaviors which were assessed were (A) initial latency in entering the dark compartment; (B) the number of compartment entries; and (C) total time spent in each compartment (FIG. 17 A, B and C). No significant difference was observed in the initial latency period prior to entry into the dark chamber. The number of crossings between the light and dark chambers was significantly increased in rats administered a high dose of CRIF ($p<0.05$). The total time spent in the light chamber was also significantly increased in these animals (i.e., those administered the high dose of CRIF) but was not affected in animals administered a low dose of CRIF or in vehicle treated animals ($p<0.05$).

The behavioral responses following icv administration indicate that this peptide has neurobehavioral effects in addition to its regulatory role in anterior pituitary ACTH and prolactin release. The increased exploratory behavior in the open field, as well as the increased activity in the light/dark box, suggest that CRIF may possess arousal properties. The increase in the time spent in the light compartment is suggestive of some anxiolytic properties in addition. Increased arousal is consistent with the increased grooming behavior in the open field induced by the peptide. Grooming is a behavior which is activated by mild stress, and considered to be related to arousal. It can be induced in non-stressed animals by electrical stimulation or peptide infusion of the periventricular region of the hypothalamus. Although grooming behavior in response to environmental events is linked to HPA activation, the pattern of the response following different types of stressors suggests that the neuroendocrine and behavioral response may be activated simultaneously by independent mechanisms.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method of treating behavioral symptoms in an anxiety disorder in a human comprising administering corticotropin release inhibiting factor to said human in an amount sufficient to alleviate said behavioral symptoms, wherein said corticotropin release inhibiting factor comprises at least three contiguous amino acids contained within the amino acid sequence positioned between the fourth and fifth thyrotropin releasing hormone sequence on a prepro-thyrotropin releasing hormone protein.

2. The method of claim 1, wherein said corticotropin release inhibitory factor comprises at least five contiguous amino acids contained within the amino acid sequence positioned between the fourth and fifth thyrotropin releasing hormone on a prepro-thyrotropin releasing hormone protein.

3. The method of claim 2, wherein said corticotropin release inhibiting factor comprises at least ten contiguous amino acids contained within the amino acid sequence positioned between the fourth and fifth thyrotropin releasing hormone on a prepro-thyrotropin releasing hormone protein.

4. The method of claim 1, wherein said corticotropin release inhibitory factor is human corticotropin release inhibitory factor.

5. The method of claim 4, wherein said corticotropin release inhibitory factor comprises the sequence Leu-Ala-Asp-Pro-Lys-Ala-Gln-Arg-Ser-Trp-Glu-Glu-Glu-Glu-Glu-Glu-Glu-Arg-Glu-Glu-Asp-Leu-Met-Pro-Glu (SEQ ID NO:2).

6. The method of claim 5, wherein said corticotropin release inhibiting factor further comprises the sequence pGlu-His-Pro-Gly-Arg-Arg (SEQ ID NO:4) at the amino terminal portion of the peptide.

7. The method of claim 1, wherein said anxiety disorder is selected from the group consisting of general anxiety disorder, panic disorder, obsessive compulsive disorder and post-traumatic stress disorder.

* * * * *

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
      (A) LENGTH: 22 amino acids
      (B) TYPE: amino acid
      (C) STRANDEDNESS: unknown
      (D) TOPOLOGY: unknown (ii) MOLECULE TYPE: peptide (xi) SEQUENCE DESCRIPTION: SEQ ID NO:1:

Phe Ile Asp Pro Glu Leu Gln Arg Ser Trp Glu Glu Lys Glu Gly Glu
1               5                  10                  15

Gly Val Leu Met Pro Glu
            20

(2) INFORMATION FOR SEQ ID NO:2:

(i) SEQUENCE CHARACTERISTICS:
        (A) LENGTH: 26 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:2:

Leu Ala Asp Pro Lys Ala Gln Arg Ser Trp Glu Glu Glu Glu Glu Glu
1               5                  10                  15

Glu Glu Arg Glu Glu Asp Leu Met Pro Glu
            20                  25

(2) INFORMATION FOR SEQ ID NO:3:

(i) SEQUENCE CHARACTERISTICS:
        (A) LENGTH: 23 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:3:

Phe Ile Asp Pro Glu Leu Gln Arg Ser Trp Glu Glu Thr Glu Gly Glu
1               5                  10                  15

Glu Gly Gly Leu Met Pro Glu
            20

(2) INFORMATION FOR SEQ ID NO:4:

(i) SEQUENCE CHARACTERISTICS:
        (A) LENGTH: 6 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:4:

Glu His Pro Gly Arg Arg
1               5

(2) INFORMATION FOR SEQ ID NO:5:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:5:

TTCATAGATC CCGAGCTCCA AAGAAGCTGG GAAGAAAAAG AGGGAGAGGG TGTCTTAATG    60

CCTGAG    66

(2) INFORMATION FOR SEQ ID NO:6:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:6:

CTGGCAGATC CCAAGGCTCA AAGGAGCTGG GAAGAAGAGG AGGAGGAGGA AGAGAGAGAG    60

GAAGACCTGA TGCCTGAA    78

(2) INFORMATION FOR SEQ ID NO:7:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:7:

TTCATAGATC CTGAGCTCCA AAGAAGCTGG GAAGAAACAG AGGGAGAGGA GGGTGGCTTA    60

ATGCCTGAG    69

(2) INFORMATION FOR SEQ ID NO:8:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:8:

-continued

```
CAACATCCAG GCCGGAGGTT CATAGATCCC GAGCTCCAAA GAAGCTGGGA AGAAAAAGAG     60

GGAGAGGGTG TCTTAATGCC TGAG                                            84

(2) INFORMATION FOR SEQ ID NO:9:

(i) SEQUENCE CHARACTERISTICS:
          (A) LENGTH: 96 base pairs
          (B) TYPE: nucleic acid
          (C) STRANDEDNESS: single
          (D) TOPOLOGY: linear
    (ii) MOLECULE TYPE: cDNA
   (iii) HYPOTHETICAL: NO
    (iv) ANTI-SENSE: NO
    (xi) SEQUENCE DESCRIPTION: SEQ ID NO:9:

CAGCACCCAG GCAGAAGGCT GGCAGATCCC AAGGCTCAAA GGAGCTGGGA AGAAGAGGAG     60

GAGGAGGAAG AGAGAGAGGA AGACCTGATG CCTGAA                               96

(2) INFORMATION FOR SEQ ID NO:10:

(i) SEQUENCE CHARACTERISTICS:
          (A) LENGTH:  87 base pairs
          (B) TYPE: nucleic acid
          (C) STRANDEDNESS: single
          (D) TOPOLOGY: linear
    (ii) MOLECULE TYPE: cDNA
   (iii) HYPOTHETICAL: NO
    (iv) ANTI-SENSE: NO
    (xi) SEQUENCE DESCRIPTION: SEQ ID NO:10:

CAGCATCCAG GCCGGAGGTT CATAGATCCT GAGCTCCAAA GAAGCTGGGA AGAAACAGAG     60

GGAGAGGAGG GTGGCTTAAT GCCTGAG                                         87

(2) INFORMATION FOR SEQ ID NO:11:

(i) SEQUENCE CHARACTERISTICS:
          (A) LENGTH:  8 amino acids
          (B) TYPE: amino acid
          (C) STRANDEDNESS: single
          (D) TOPOLOGY: linear
    (ii) MOLECULE TYPE: peptide
   (iii) HYPOTHETICAL: NO
    (iv) ANTI-SENSE: NO
    (xi) SEQUENCE DESCRIPTION: SEQ ID NO:11:

Lys Arg Gln His Pro Gly Lys Arg
1               5
```